United States Patent
Lockwood et al.

(10) Patent No.: US 10,653,750 B2
(45) Date of Patent: May 19, 2020

(54) USE OF CCL2 TO INHIBIT ABNORMAL UTERINE BLEEDING

(71) Applicant: UNIVERSITY OF SOUTH FLORIDA, Tampa, FL (US)

(72) Inventors: Charles Joseph Lockwood, Tampa, FL (US); Umit Ali Kayisli, Wesley Chapel, FL (US); Murat Basar, New Haven, CT (US); Ozlem Guzeloglu-Kayisli, Wesley Chapel, FL (US); Nihan Semerci, Tampa, FL (US); Frederick Schatz, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/561,158

(22) PCT Filed: Mar. 23, 2016

(86) PCT No.: PCT/US2016/023811
§ 371 (c)(1),
(2) Date: Sep. 25, 2017

(87) PCT Pub. No.: WO2016/154335
PCT Pub. Date: Sep. 29, 2016

(65) Prior Publication Data
US 2018/0078615 A1    Mar. 22, 2018

Related U.S. Application Data

(60) Provisional application No. 62/137,092, filed on Mar. 23, 2015.

(51) Int. Cl.
| | | |
|---|---|---|
| *A61K 38/19* | (2006.01) | |
| *A61K 45/06* | (2006.01) | |
| *A61K 31/57* | (2006.01) | |
| *A61P 15/00* | (2006.01) | |
| *A61K 9/00* | (2006.01) | |

(52) U.S. Cl.
CPC ............ *A61K 38/195* (2013.01); *A61K 31/57* (2013.01); *A61K 45/06* (2013.01); *A61P 15/00* (2018.01); *A61K 9/0024* (2013.01)

(58) Field of Classification Search
None
See application file for complete search history.

(56) References Cited

U.S. PATENT DOCUMENTS

2010/0305210 A1    12/2010 Barkan et al.

FOREIGN PATENT DOCUMENTS

WO   WO 2013/090321   6/2013

OTHER PUBLICATIONS

Selzman et al, American Journal of Physiology Heart and Circulatory Physiology, vol. 283, pp. H1455-H1461.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Anderson W, Nature, 1998. vol. 392, pp. 25-30.*
Verma et al. Nature, 1997. vol. 389, p. 239-242.*
Crystal R, Science, 1995. vol. 270, pp. 404-410.*
Gabor M. Rubanyi , Mol Aspects Med , 2001 vol. 22, pp. 113-142.*
Eck et al. (Goodman & Gilnnan's The Pharmacological Basis of Therapeutics (1996), 9th Edition, Chapter 5, McGraw-Hill, NY, pp. 77-101).*
Marshall, Science, 1995, vol. 269, pp. 1050-1055.*
Juengst et al, British Medical Journal; 2003, vol. 326, pp. 1410-1411.*
Li et al, Molecular and Cellular Biochemistry; 1993, vol. 126, pp. 61-68.*
Shobeiri et al, Phytotherapy Research, 2009; vol. 23, pp. 1411-1414.*
Abberton, K. M. et al. "Vascular smooth muscle cell proliferation in arterioles of the human endometrium" *Human Reproduction*, 1999, 14(4):1072-1079.
Affandi, B. "Long-acting progestogens" *Best Practice & Research: Clinical Obstetrics & Gynaecology*, 2002, 16(2):169-179.
Attar, R. et al. "Association of CCL2 and CCR2 Gene Variants with Endometrial Cancer in Turkish Women" In vivo, 2010, 24: 243-248.
Collins, J. et. al. "Hormonal contraception without estrogens" *Human Reproduction Update*, 2003, 9(4):373-386.
Guzeloglu-Kayisli, O. et al. "Long-Acting Progestin-Only Contraceptives Enhance Human Endometrial Stromal Cell Expressed Neuronal Pentraxin-1 and Reactive Oxygen Species to Promote Endothelial Cell Apoptosis" *The Journal of Clinical Endocrinology & Metabolism*, Oct. 2014, 99(10):1-21.
Hayes, I. M. et al. "Human Vascular Smooth Muscle Cells Express Receptors for CC Chemokines" *Arteriosclerosis, Thrombosis, and Vascular Biology*, 1998, 18(3):397-403.
Hellström, M. et al. "Role of PDGF-B and PDGFR-β in recruitment of vascular smooth muscle cells and pericytes during embryonic blood vessel formation in the mouse" *Development*, 1999, 126(14):3047-3055.

(Continued)

*Primary Examiner* — Joanne Hama
*Assistant Examiner* — Fozia Hamud
(74) *Attorney, Agent, or Firm* — Saliwanchik, Lloyd & Eisenschenk

(57) ABSTRACT

The present invention concerns compositions and methods for inhibition of abnormal uterine bleeding (AUB), such as that associated with use of long-acting progestin-only contraceptives (LAPCs). An aspect of the invention concerns compositions comprising chemokine (C-C motif) ligand 2 (CCL2), or a biologically active fragment thereof, which may administered to subjects for inhibition of AUB. Another aspect of the invention concerns methods for inhibiting AUB, comprising administering an effective amount of CCL2, or a biologically active fragment thereof, to a subject in need thereof. Another aspect of the invention concerns a kit for inhibiting AUB.

13 Claims, 11 Drawing Sheets
Specification includes a Sequence Listing.

(56) References Cited

OTHER PUBLICATIONS

Hickey, M. et al. "Superficial endometrial vascular fragility in Norplant users and in women with ovulatory dysfunctional uterine bleeding" *Human Reproduction*, 2000, 15(7):1509-1514.

Hickey, M. et al. "Long-Term Progestin-Only Contraceptives Result in Reduced Endometrial Blood Flow and Oxidative Stress" *The Journal of Clinical Endocrinology & Metabolism*, 2006, 91(9):3633-3638.

Hu, X. et al. "IFN-γ-Primed Macrophages Exhibit Increased CCR2-Dependent Migration and Altered IFN-γ Responses Mediated by Stat1" *The Journal of Immunology*, 2005, 175(6):3637-3647.

Kayisli, U. A. et al. "Long-acting progestin-only contraceptives impair endometrial vasculature by inhibiting uterine vascular smooth muscle cell survival" *PNAS*, Apr. 25, 2015, 112(16):5153-5158.

Kim, D- K. et al. "H19, a Developmentally Regulated Gene, Is Reexpressed in Rat Vascular Smooth Muscle Cells After Injury" *Journal of Clinical Investigation*, Jan. 1994, 93(1):355-360.

Krikun, G. et al. "Long-term progestin contraceptives (LTPOC) induce aberrant angiogenesis, oxidative stress and apoptosis in the guinea pig uterus: A model for abnormal uterine bleeding in humans" *Journal of Angiogenesis Research*, 2010, 2:1-7.

Krikun, G. et al. "Long-term progestin-only contraception in humans versus animal models" *Annals of the New York Academy of Sciences*, 2011, 1221:119-123.

Krikun, G. et al. "Effects of Etonogestrel Treatment in the Reproductive Organs and Uterine Arteries of Nonoophorectomized Guinea Pigs" *Reproductive Sciences*, 2012, 19(4):400-406.

Lash, G. E., et al. "Localization of angiogenic growth factors and their receptors in the human endometrium throughout the menstrual cycle and in recurrent miscarriage" *Human Reproduction*, 2012, 27(1):183-195.

Lee, W. S. et al. "Progesterone inhibits arterial smooth muscle cell proliferation" *Nature Medicine*, 1997, 3(9):1005-1008.

Levéen, P. et al. "Mice deficient for PDGF B show renal, cardiovascular, and hematological abnormalities" *Genes & Development*, 1994, 8(16):1875-1887.

Livingstone, M. et al. "Mechanisms of abnormal uterine bleeding" *Human Reproduction Update*, 2002, 8(1):60-67.

Lockwood, C. J. Mechanisms of Normal and Abnormal Endometrial Bleeding. *Menopause*, Apr. 1, 2011, 18(4):408-411.

Lockwood, C. J. et al. "Interferon-γ Protects First-Trimester Decidual Cells Against Aberrant Matrix Metalloproteinases 1, 3, and 9 Expression in Preeclampsia" *The American Journal of Pathology*, Sep. 2014, 184(9):2549-2559.

Lockwood, C. J. et al. "Decidualized Human Endometrial Stromal Cells Mediate Hemostasis, Angiogenesis, and Abnormal Uterine Bleeding" *Reproductive Sciences*, Feb. 2009, 16(2):162-170.

Lockwood, C. J. et al. "Angiogenic factors and the endometrium following long term progestin only contraception" *Histology and Histopathology*, 2004, 19(1):167-172.

Rogers, P. A. W. et al. "Perivascular smooth muscle α-actin is reduced in the endometrium of women with progestin-only contraceptive breakthrough bleeding" *Human Reproduction*, 2000, 15(Suppl 3):78-84.

Rogers, P. A. W. et al. "Endometrial Arteriogenesis: Vascular Smooth Muscle Cell Proliferation and Differentiation During the Menstrual Cycle and Changes Associated With Endometrial Bleeding Disorders" *Microscopy Research and Technique*, 2003, 60:412-419.

Semerci, N. et al. "Whole Genome Analysis of Long-Acting Progestin Only Contraceptive Treated Vascular Smooth Muscle Cells Identifies Suppression of CCL2 mediated STAT1 signaling in Inducing Abnormal Uterine Bleeding" presented at Society for Reproductive Investigations 62nd Annual Meeting, San Francisco, CA, Mar. 25-28, 2015 (abstract and poster).

Soriano, P. "Abnormal kidney development and hematological disorders in PDGF β-receptor mutant mice" *Genes & Development*, 1994, 8(16):1888-1896.

Spinetti, G. et al. "Rat Aortic MCP-1 and Its Receptor CCR2 Increase With Age and Alter Vascular Smooth Muscle Cell Function" *Arteriosclerosis, Thrombosis, and Vascular Biology*, 2004, 24(8):1397-1402.

Tanaka, K. et al. "Interaction of Tmem119 and the bone morphogenetic protein pathway in the commitment of myoblastic into osteoblastic cells" *Bone*, 2012, 51(1):158-167.

Watanabe, T. et al. "Monocyte chemotactic protein 1 amplifies serotonin-induced vascular smooth muscle cell proliferation" *The Journal of Vascular Research*, 2001, 38(4):341-349.

\* cited by examiner

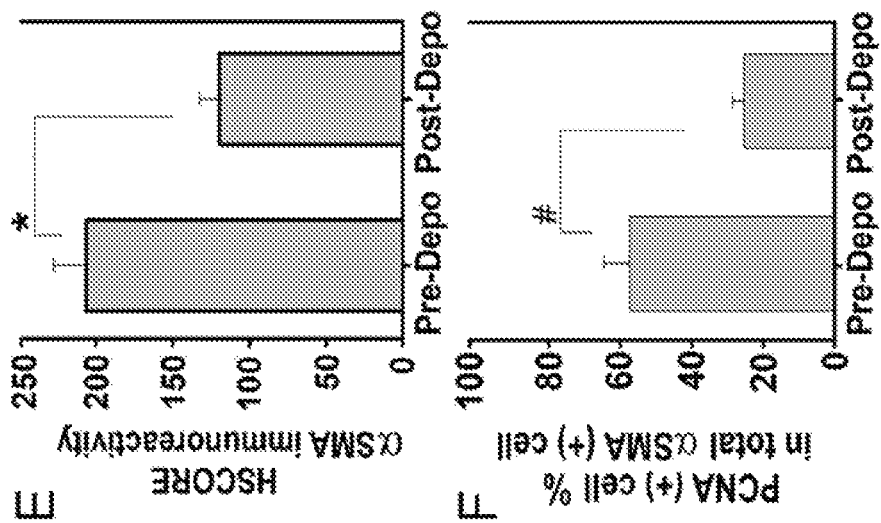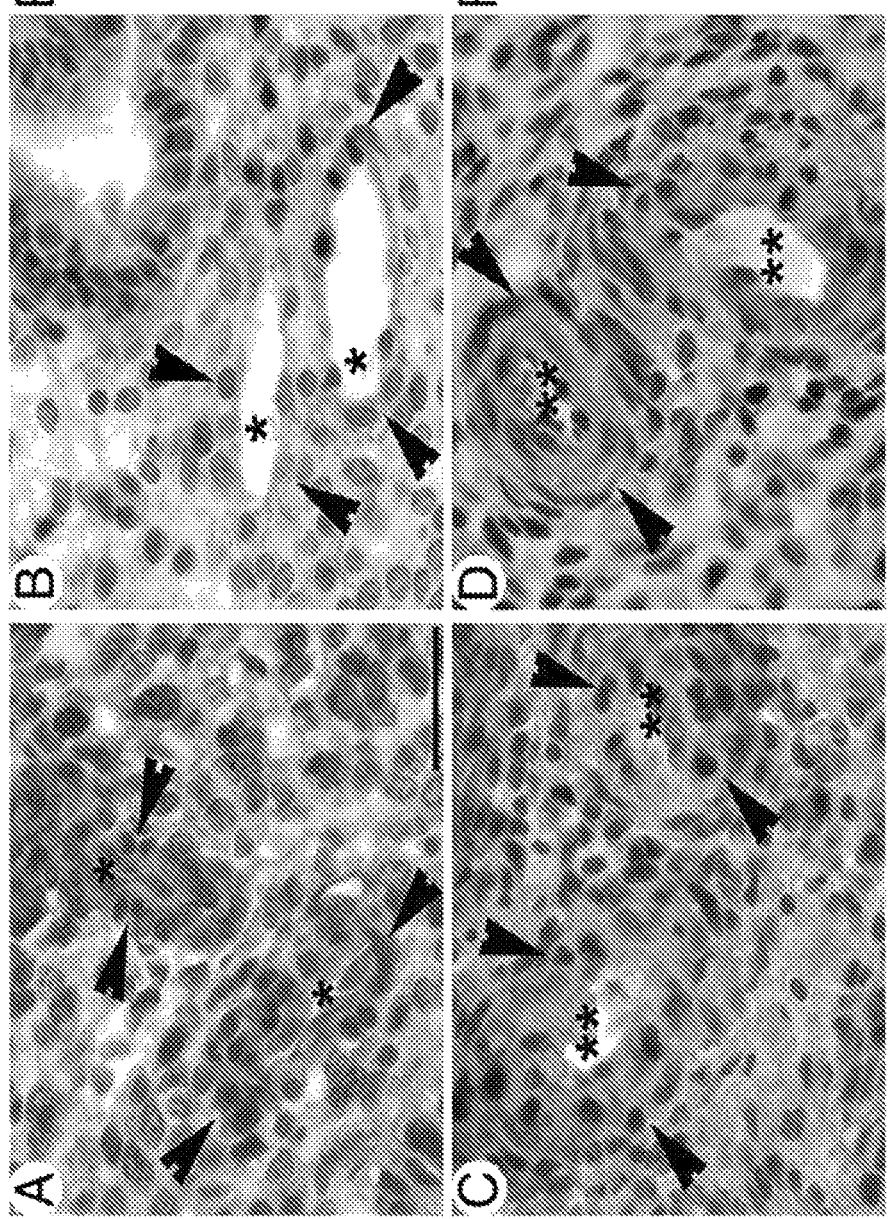

FIG. 2B
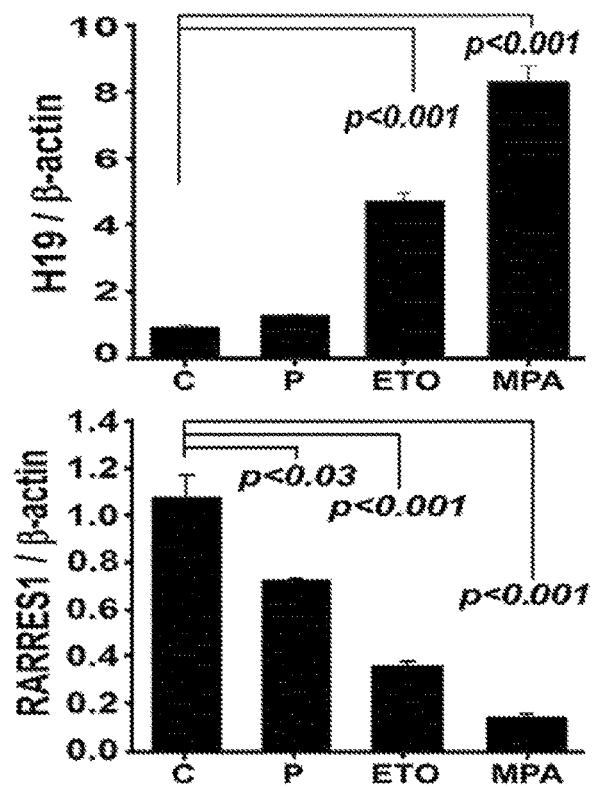
FIG. 2C
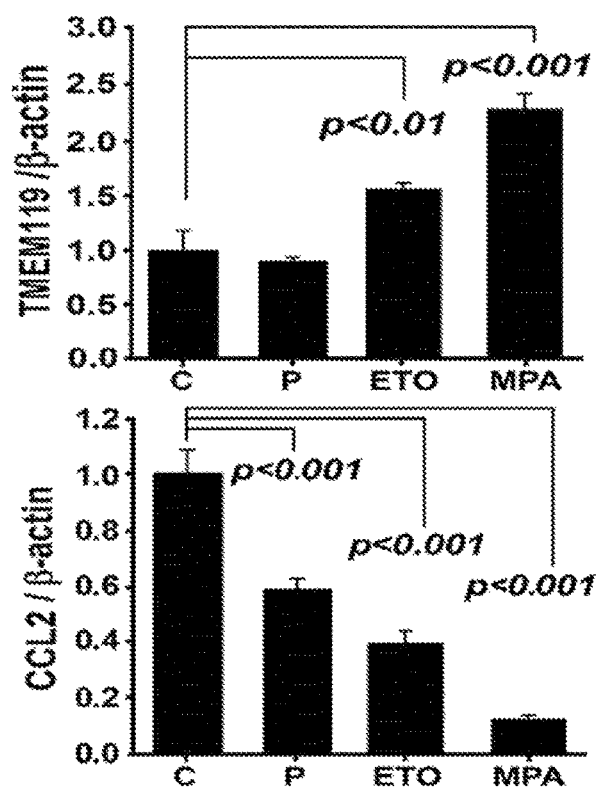
FIG. 2D
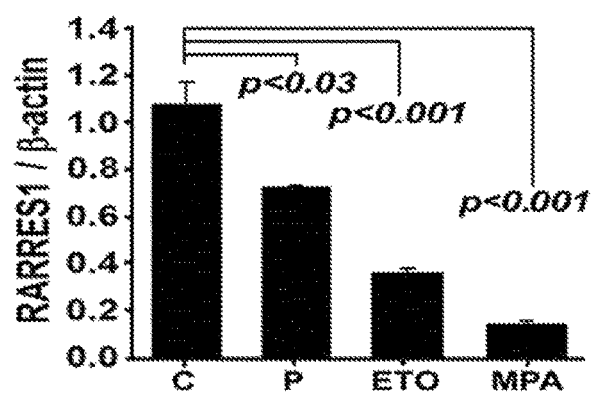
FIG. 2E
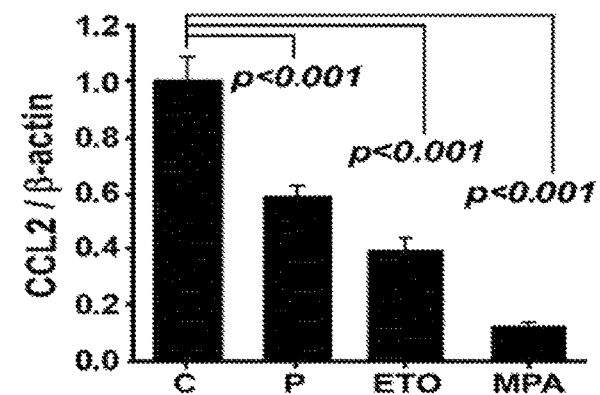
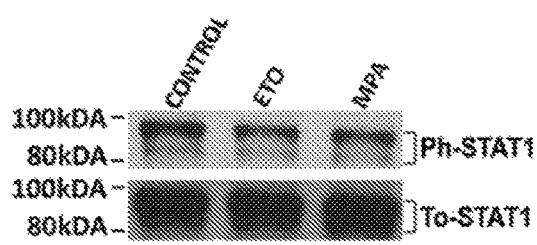
FIG. 3B

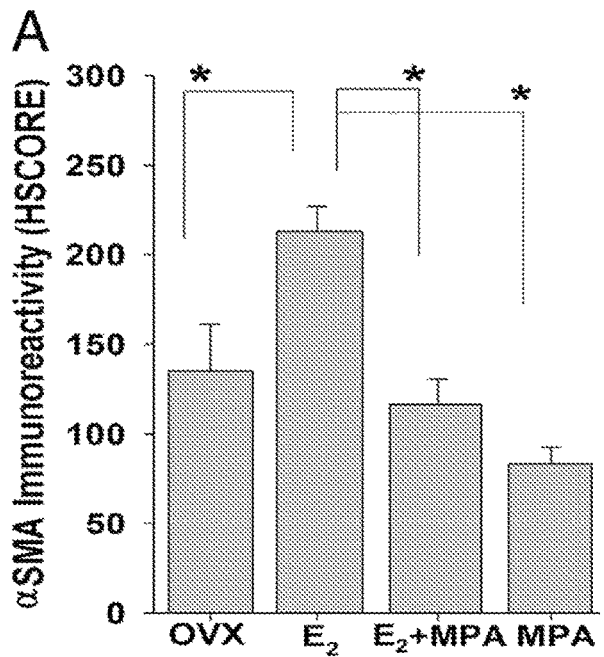
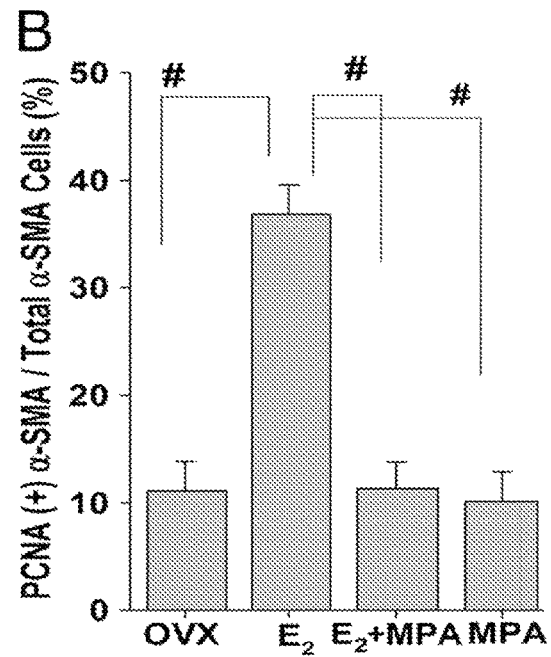
FIG. 7A    FIG. 7B
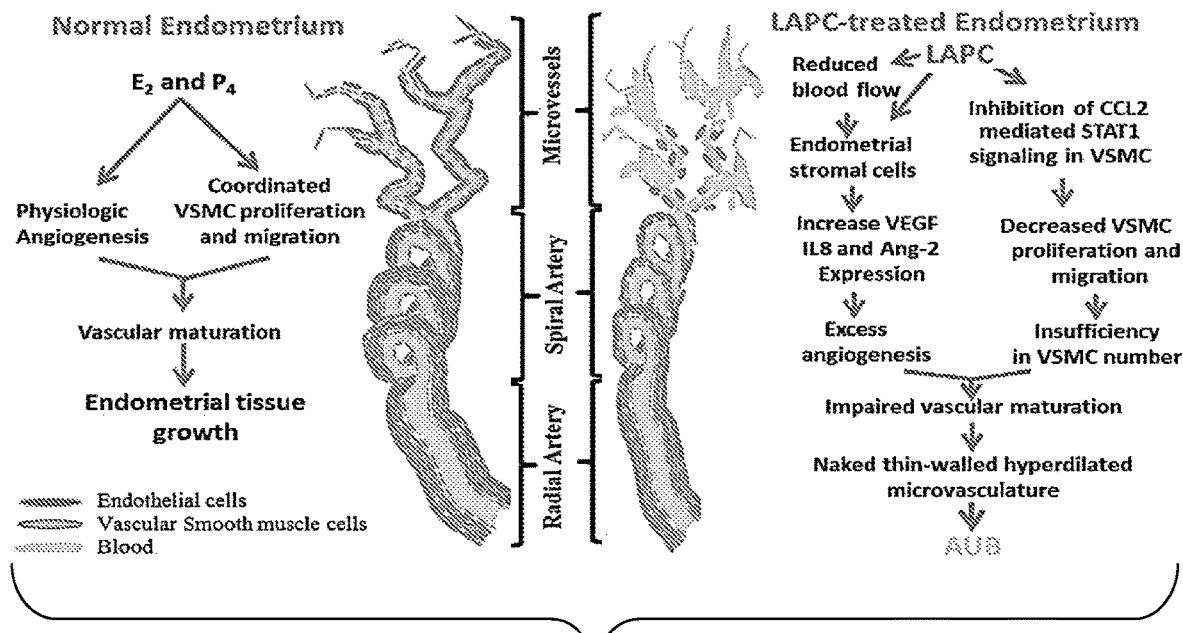
FIG. 8

USE OF CCL2 TO INHIBIT ABNORMAL UTERINE BLEEDING

CROSS-REFERENCE TO RELATED APPLICATIONS

The present application is the National Stage of International Application No PCT/US2016/023811 filed Mar. 23, 2016, which claims the benefit of U.S. Provisional Application Ser. No. 62/137,092, filed Mar. 23, 2015, each of which is hereby incorporated by reference herein in its entirety, including any figures, tables, nucleic acid sequences, amino acid sequences, or drawings.

GOVERNMENT SUPPORT

This invention was made with government support RO1 HD033937 awarded by the National Institutes of Health. The government has certain rights in the invention.

BACKGROUND OF THE INVENTION

Over a million unintended pregnancies occur in the USA each year because of either discontinuation or misuse of contraceptives. Long-acting progestin-only contraceptives (LAPC) sub-dermal implants and intrauterine devices are ideal contraceptives since they are long acting, do not require strict adherence to a daily pill, or the discomfort of a patch or vaginal ring and because they are free from the thrombotic risks attendant estrogen-containing combined hormonal contraceptives. However, the major reason for discontinuation of LAPCs is the occurrence of unpredictable, intermittent, abnormal uterine bleeding (AUB). Discovering molecular/cellular targets that contribute to LAPC-induced AUB is essential to creating better contraceptive formulations.

BRIEF SUMMARY OF THE INVENTION

The inventors found that two progestin agents used in LAPCs, medroxyprogesterone acetate (MPA) and etonogestrel (ETO) reduce proliferation of human and guinea pig endometrial vascular smooth muscle cells (VSMCs) resulting in production of thin-walled hyperdilated fragile microvessels that are prone to bleed. Microarray analysis of cultured VSMCs treated with MPA or ETO revealed that the chemokine (C-C motif) ligand 2 (CCL2) was inhibited by these progestins. In VSMC cultures, MPA and ETO inhibited VSMC proliferation and administration of recombinant CCL2 (rCCL2) reversed this LAPC effect. Taken together, these findings suggest that LAPCs impair endometrial vascular integrity by inhibiting VSMC proliferation and that concomitant CCL2 administration may reduce (alleviate) or prevent LAPC-induced AUB.

BRIEF DESCRIPTION OF THE DRAWINGS

FIGS. 1A-1F. Reduced αSMA and PCNA immunoreactivity in VSMCs of endometria of women receiving Depo-Provera (Depo, Depot medroxyprogesterone acetate). Immunoreactivity for αSMA (red) and PCNA (brown) in VSMCs (arrowheads) surrounding pre-(FIG. 1A) vs. post-Depo (FIG. 1B) endometrial microvessels (single asterisk denotes lumen); and pre-(FIG. 1C) vs. post-Depo (FIG. 1D) endometrial spiral arteries (double asterisks denote lumen). Note reduced αSMA immunoreactivity and fewer PCNA (+) cells among VSMCs in post-Depo administered endometria (FIG. 1B and FIG. 1D) vs. their corresponding pairs (FIG. 1A and FIG. 1C). Graphs display αSMA HSCOREs (FIG. 1E) and percentage of PCNA positively stained nuclei (FIG. 1F) in VSMCs. Bars (n=6) represent mean±SEM; *P<0.008 and # P<0.003. (Scale bar, 40 μm).

FIGS. 2A-2E. Differentially regulated genes in VSMCs by progestins. Venn diagram analysis of genes regulated individually or in common by MPA or ETO or $P_4$ (FIG. 2A). qRT-PCR analysis for regulation of H19, TMEM119, RARRES1, and CCL2 mRNA in cultured VSMC by progestins (FIGS. 2B-2E). Bars represent mean±SEM (n=3). C, control; P, progesterone ($P_4$).

FIGS. 3A-3B. MPA and ETO inhibit STAT1 signaling in VSMCs. IPA identified a cluster of differentially regulated genes by MPA (Left) or ETO (Right) associated with inhibition of STAT1 signaling (FIG. 3A). Immunoblotting of total (To-) and phosphorylated (Ph-) STAT1 in VSMCs treated with control, ETO and MPA for 15 min (FIG. 3B). All gene symbols were abbreviated according to GenBank standard nomenclature.

FIGS. 7A-7B. Semiquantitative analysis of αSMA and PCNA immunoreactivity in endometrium of OVX GPs. Graphs represents HSCORE values for αSMA expression (A) and percentage of PCNA (+) VSMCs (B). Bars represent mean±SEM; n=6 for each group; *P<0.005 or # P<0.001.

FIG. 8. Model of aberrant vascular transformation and related AUB in women administered LAPCs. In normal endometrium, estradiol ($E_2$) and progesterone ($P_4$) regulate angiogenesis as well as VSMC proliferation and migration. Coordination of these steroid-mediated effects triggers vascular maturation resulting in a tight and continuous layer of VSMCs lying beneath endothelial cells of new vessels, which provides normal blood flow to induce endometrial growth. In contrast, long-term effects on human endometrium by synthetic progestins elicit: (i) reduced blood flow which induces local hypoxia; (ii) induced decidualization and increased expression of such angiogenic factors as VEGF, IL8, and Ang-2 in stromal cells; and (iii) inhibited VSMC proliferation and migration by blocking CCL2-mediated STAT1 signaling. The first two mechanisms promote excess angiogenesis, whereas the third mechanism results in insufficient VSMC numbers to cover and surround newly formed vessels. Consequently, impaired vascular maturation generates thin-walled hyperdilated fragile vessels which are prone to leakage and AUB.

FIGS. 9A-1, 9A-2, 9B-1, and 9B-2. LAPCs do not alter apoptotic index in cultured VSMCs. Cleaved caspase-3 immunoreactivity (arrows) (FIG. 9A-1) and nuclear fragments (arrowheads) in FITC-conjugated phalloidin and DAPI double-stained (FIG. 9B-1) in VSMC cultures. Bars (mean±SEM) represent numbers of cleaved caspase-3 immunoreactive cells or nuclear fragments in VSMC cultures treated with vehicle (control) or $10^{-7}$ M of $P_4$, ETO, or MPA for 48 h under 40× objective magnification. P>0.05 for comparison between any treatment conditions.

DETAILED DESCRIPTION OF THE INVENTION

Figure 2A:
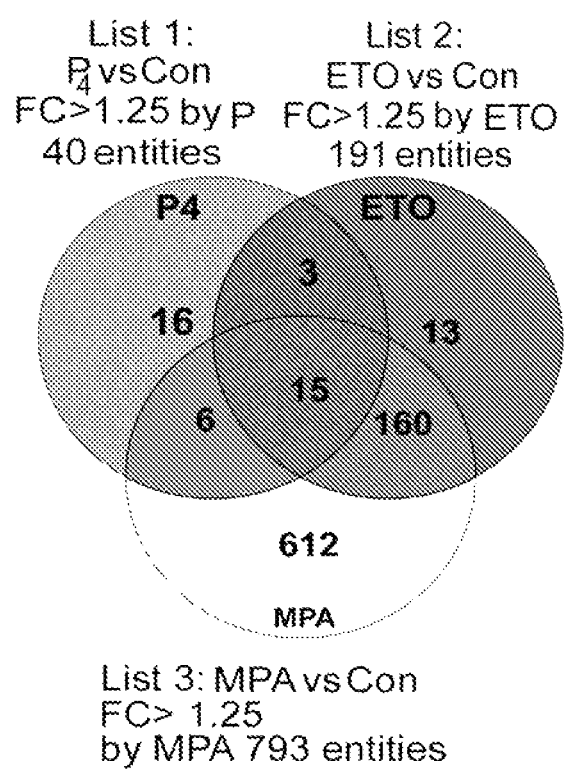

Over a million unintended pregnancies occur in the USA each year because of either discontinuation or misuse of contraceptives. An ideal contraceptive method is safe, discrete and effective and does not require the involvement of trained medical personnel. Long-acting progestin-only contraceptives (LAPCs) meet these criteria and can be used by women in whom estrogen use is contraindicated (1, 2). Currently available LAPCs include Depo-Provera (Depo), medroxyprogesterone acetate (MPA), and the Implanon device (3). The major reason for discontinuation of LAPCs is the occurrence of unpredictable, abnormal uterine bleeding (AUB).

LAPC-associated AUB occurs intermittently and focally from irregularly distributed superficial, enlarged, thin-walled vessels. The cellular mechanisms responsible for these irregular changes are unknown with the exception of abnormal angiogenesis.

Completion of angiogenesis requires functional maturation of newly formed vessels involving formation of a perivascular coat resulting from trans-differentiation of mural cells to either pericytes or vascular smooth muscle cells (VSMCs) (37, 11). The contractile state of mural cells maintains vascular tone, a critical determinant of vessel volume and local blood flow. Both VSMCs and pericytes express common molecular markers such as α-smooth muscle actin (α-SMA) and tropomyosin (38, 39).

The current study postulates that administration of LAPCs suppresses differentiation, proliferation and/or migration of VSMCs and/or pericytes, which prevents tight coupling with endothelial cells in newly formed vessels resulting in generation of bare thin-walled hyper-dilated vessels that are prone to bleed.

Discovering the molecular/cellular targets that contribute to LAPC-induced AUB is essential to developing newer agents that prevent AUB and reduce discontinuation rates. During each menstrual cycle endometrium undergoes re-vascularization and vascular maturation to successfully rebuild the functional layer of endometrium. In contrast, the inventors found that women using LAPCs display impaired endometrial vascular maturation that in turn induces vascular leakage and AUB. These side effects of LAPCs were confirmed by cell culture and animal studies. Further studies using whole genome analyses identified a molecule, the chemokine (C-C motif) ligand 2 (CCL2), whose recombinant human protein form holds promise to prevent AUB in women using LAPCs.

Molecular mechanisms responsible for abnormal endometrial vasculature in women receiving LAPCs are unknown. The inventors hypothesize that LAPCs impair vascular smooth muscle cell (VSMC) and pericyte proliferation and migration producing thin-walled hyperdilated fragile microvessels prone to bleeding. Proliferating cell nuclear antigen (PCNA) and α-smooth muscle actin (αSMA) double-immunostaining assessed VSMC differentiation and proliferation in endometria from women before and after DepoProvera (Depo) treatment and from oophorectomized guinea pigs (OVX-GPs) treated with vehicle, estradiol (E2), medroxyprogesterone acetate (MPA), or E2+MPA. Whole-genome profiling, proliferation, and migration assays were performed on cultured VSMCs treated with MPA or etonogestrel (ETO). Endometrial vessels of Depo-administered women displayed reduced αSMA immunoreactivity and fewer PCNA (+) nuclei among αSMA (+) cells (P<0.008). Microarray analysis of VSMCs identified several MPA- and ETO-altered transcripts regulated by STAT1 signaling (P<$2.22 \times 10^{-6}$), including chemokine (C-C motif) ligand 2 (CCL2). Both MPA and ETO reduce VSMC proliferation and migration (P<0.001). Recombinant CCL2 reversed this progestin-mediated inhibition, whereas a STAT1 inhibitor abolished the CCL2 effect. Similarly, the endometria of MPA treated OVX-GPs displayed decreased αSMA staining and fewer PCNA (+) nuclei in VSMC (P<0.005). In conclusion, LAPCs promote abnormal endometrial vessel formation by inhibiting VSMC proliferation and migration.

LAPCs are safe, discrete, effective, and can be used by women in whom estrogen use is contraindicated (1, 2). However, associated abnormal uterine bleeding (AUB) reduces adherence (1-3). The endometria of women receiving LAPCs contain elevated levels of VEGF and angiopoietin-2 (Ang-2) (4). Like women, the guinea pig (GP) exhibits spontaneous estrous cycling and hemochorial placentation (5-7) and is a relevant animal model to study LAPC-induced AUB (1, 8-10). In humans and GPs, this hyperangiogenic milieu creates endometria displaying superficial, irregularly distributed enlarged, thin-walled capillaries and venules (2, 9, 10). Vascular smooth muscle cells (VSMCs) and pericytes maintain vascular tone, a critical determinant of vessel volume and blood flow (11). Endothelial cells of arteries and veins are surrounded by VSMCs, whereas those of capillaries are surrounded Q:11 by pericytes (12). Completion of angiogenesis requires envelopment of new vessels by pericytes or VSMCs, which express α-smooth muscle actin (αSMA) and tropomyosin (11-13).

Currently available LAPCs include Depo, an injectable form of MPA, and Implanon, a subdermally implanted rod that releases etonogestrel (ETO) (3). Women administered LAPCs display significantly reduced endometrial blood flow (14), consistent with constriction of uterine arteries and arterioles. Although ETO administration constricts GP uterine radial arteries (8), it paradoxically induces hyperdilation in microvasculature in the functional endometrium (2, 9, 10). The inventors postulate that LAPCs suppress VSMC and pericyte differentiation, proliferation, and migration to create fragile, thin-walled hyperdilated vessels prone to bleed.

LAPCs trigger formation of irregularly distributed superficial, enlarged, thin-walled endometrial capillaries and venules that cause AUB. Molecular mechanisms responsible for these LAPC induced abnormal endometrial vascular changes are unknown. The inventors found that suppression of endometrial vascular smooth muscle cell (VSMC) proliferation in LACP users, which impairs endometrial vascular maturation and causes thin-walled and hyperdilated vasculature. The inventors investigated molecules and signaling pathways regulating LAPC mediated suppression of VSMC proliferation.

Cultured VSMCs (n=3) treated with control medium or medium containing medroxyprogesterone acetate (MPA, $10^{-7}$ M), or etonogestrel (ETO, $10^{-7}$ M) were processed for whole genome analyses using Illumina Human microarray kit. After qRT-PCR confirmation of several up and down regulated genes from microarray data, Ingenuity Pathway Analysis (IPA) determined relevant upstream signaling of LAPC altered gene expression. To investigate the role of genes and relevant signaling molecules identified by IPA, VSMCs (n=3) treated with MPA or ETO±1 or 10 ng/ml recombinant CCL2 (rCCL2)±STAT1 inhibitor, 5'-methylthioadenosine (MTA, 100 μM) were analyzed by BrdU incorporation proliferation, TUNEL based ELISA apoptosis and Transwell insert migration assays.

Microarray and qRT-PCR analyses revealed significant inhibition of CCL2 expression in MPA or ETO treated VSMCs (p<0.001). IPA of microarray results identified STAT1 (p<0.000025) as a common signaling molecule mediator of MPA or ETO altered gene expression. Both MPA and ETO reduced proliferation and migration in VSMCs (p<0.001), but did not affect the apoptosis index. Addition of rCCL2 reversed inhibition by LAPC (p<0.01); MTA abolished this CCL2 effect in VSMC cultures (p<0.01).

These results reveal a unique cellular and molecular mechanism by which LAPCs suppress endometrial VCMS proliferation and migration by inhibiting CCL2-induced STAT1 signaling, that explains the resulting generation of thin-walled hyperdilated endometrial vessels in LAPC users. Administration of CCL2 and/or development of new agents that target endometrial VSMCs may reduce/prevent LAPC-induced AUB.

In some embodiments, the subject is suffering from inflammation such as that associated with a medical condition selected from the group consisting of cancer, autoimmune, hypersensitivity, diabetes, infectious, transplantation associated and allergy. In some embodiments, the subject is not suffering from inflammation such as that associated with a medical condition selected from the group consisting of cancer, autoimmune, hypersensitivity, diabetes, infectious, transplantation associated and allergy.

Without being limited by theory, it is postulated that administration of LAPCs suppresses differentiation, proliferation, and/or migration of vascular smooth muscle cells (VSMC), and/or pericytes, which prevents tight coupling with endothelial cells in newly formed vessels resulting in generation of bare thin-walled hyper-dilated vessels that are prone to bleed.

The chemokine (C-C motif) ligand 2 (CCL2) is also referred to as monocyte chemotactic protein 1 (MCP1). The amino acid sequence of human CCL2 is known (see, for example, "Deshmane S L et al., "Monocyte Chemoattractant Protein-1 (MCP-1): An Overview", *Journal of Interferon & Cytokine Research*, 29, 2009; NCBI Reference Sequence: NP_002973.1, which is each incorporated herein by its entirety. The human CCL2 amino acid sequence is MKVSAALLCLLLIAATFIPQGLAQPDAINAPVTCCY NFTNRKISVQRLASYRRITS SKCPKEAVIFKTIVAKEI CADPKQKWVQDSMDHLDKQTQTPKT (SEQ ID NO:1), with the signal sequence underlined.

CCL2 may be administered as a precursor (with its 23-amino acid signal peptide) or in its mature form.

CCL2 may be administered in glycosylated or non-glycosylated form.

Biologically active fragments of full-length CCL2 may be administered.

In some embodiments, the CCL2 is the amino acid sequence of SEQ ID NO:1 (human precursor CCL2), amino acids 24-99 of SEQ ID NO:1 (human mature CCL2), or a biologically active fragment or variant of either.

Biologically active CCL-2 variant polypeptides having at least 70% amino acid sequence identity to the normal, wild-type sequence, and which retain the ability to inhibit AUB, may be administered. For example, CCL2 variant polypeptides may have 70%, 75%, 80%, 85%, 90%, 95%, 96%, 97%, 98%, or 99% sequence identity with the human MCP-1 polypeptide. Biologically active fragments of CCL2 are sub-sequences of the full-length CCL2 polypeptide. For example, the biologically active fragment of CCL2 may be 35, 36, 37, 38, 39, 40, 41, 42, 43, 44, 45, 46, 47, 48, 49, 40, 51, 52, 53, 54, 55, 56, 57, 58, 59, 60, 61, 62, 63, 64, 65, 66, 67, 68, 69, 70, 71, 72, 73, 74, or 75 contiguous amino acids of the mature, full-length (76 amino acid) human MCP-1 polypeptide. In some embodiments, the CCL2 administered is full-length human MCP-1 or a biologically fragment or variant thereof that includes a first region spanning Thr-10 to Tyr-13 and a second region spanning residues 34 and 35. Mutational analysis of CCL2 resulted in the identification of regions important to chemokine function and cell-type specificity (see Beall C J et al., "Site-directed mutagenesis of monocyte chemoattractant protein-1 identifies two regions of the polypeptide essential for biological activity," Biochem J 313:633-640, 1996, which is incorporated herein by reference in its entirety).

CCL2 fragments and variants are biologically active in the sense that they retain the activity of the normal, full-length, wild-type sequence to inhibit AUB. This may be evaluated in vitro or in vivo, for example, by assessing whether the fragment or variant is capable of partially or fully reversing LAPC-mediated inhibition of differentiation, proliferation, and/or migration of vascular smooth muscle cells (VSMC) and/or pericytes (e.g., via STAT1 signaling).

The CCL2 protein may be administered in glycosylated or unglycosylated form.

The CCL2 of the present invention can be administered to the subject per se, or in a pharmaceutical composition where it is mixed with suitable carriers or excipients.

As used herein, the term "subject" refers to a female, human or non-human mammal. In some embodiments, the subject is a human female. The subject may be any age. In some embodiments, the subject is a post-pubescent female. In some embodiments, the subject is one diagnosed with abnormal uterine bleeding, or is at risk of abnormal uterine bleeding at the time of administering CCL2. In some embodiments, the subject is taking an LAPC at the time of administering CCL2.

As used herein, a "pharmaceutical composition" refers to a preparation of one or more of the active ingredients described herein (e.g., CCL2 polypeptide or nucleic acid encoding CCL2) with other components such as physiologically suitable carriers and excipients. The purpose of a pharmaceutical composition is to facilitate administration of an agent to the subject.

As used herein, the term "active ingredient" refers to the CCL2 accountable for the intended biological effect. The CCL2 (e.g., human, full-length, wild-type CCL2, or biologically active fragments or variants thereof), may be administered as a polypeptide or as a nucleic acid encoding the CCL2 (via gene delivery), which is then expressed in the subject. Nucleic acids encoding CCL2 may be administered in a viral or non-viral vector, and may be operably linked to control sequences to direct expression of the nucleic acid encoding CCL.

As used herein, the phrases "physiologically acceptable carrier" and "pharmaceutically acceptable carrier," which may be used interchangeably, refer to a carrier or a diluent that does not cause significant irritation to the subject and does not abrogate the biological activity and properties of the administered agent.

As used herein, the term "excipient" refers to an inert substance added to a pharmaceutical composition to further facilitate administration of an active ingredient. Examples of excipients include, but are not limited to, calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, intravaginal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a subject.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. The CCL2 may be produced by various methods, e.g., synthetically or recombinantly. Human recombinant CCL2 (Cat. GF012) is commercially available from EMD Millipore (Billerica, Mass., USA); and R&D Systems (cat. no. 279-MC; Minneapolis, Minn., USA). Such protein products may be suitable for formulating pharmaceutical composition comprising the CCL2 protein.

Pharmaceutical compositions may be in the form of a patch, implant (e.g., subdermal implant), intrauterine device, or vaginal ring. Intrauterine devices typically include a frame and retention elements for retaining the frame within the uterus. Such devices are often "T"-shaped.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated may be used in the formulation. Such penetrants are generally known in the art.

For oral administration, the pharmaceutical composition can be formulated readily by combining the active ingredient(s) with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, an "effective amount" means an amount of active ingredients (e.g., CCL2) effective to prevent, delay onset of, alleviate, or ameliorate symptoms of a disorder (e.g., abnormal uterine bleeding (AUB)), e.g., by partially or fully reversing LAPC suppression of differentiation, proliferation, and/or migration of VSMCs and/or pericytes, or by a different mechanism.

Determination of an effective amount is well within the capability of those skilled in the art, especially in light of the detailed disclosure provided herein.

For any preparation used in the methods of the invention, the dosage or the effective amount can be estimated initially from in vitro and cell culture assays (e.g., proliferation assay as further described herein below). For example, a dose can be formulated in animal models to achieve a desired concentration or titer. Such information can be used to more accurately determine useful doses in humans.

The present invention also includes a kit for inhibiting abnormal uterine bleeding, comprising chemokine (C-C motif) ligand 2 (CCL2), or a biologically active fragment thereof; and (a) a long-acting progestin-only contraceptive, or (b) another agent that inhibits abnormal uterine bleeding, or both (a) and (b), optionally with reagents and/or instructions for use. The CCL2, or a biologically active fragment thereof, of the kit may be formulated for any administration route, as described herein (e.g., oral, injectable, or transdermal delivery), and may be included as a component within a pharmaceutical composition. Preferably, an effective amount of CCL2, or a biologically active fragment thereof, is included in the kit.

Generally, the kit comprises a container and a label or package insert on or associated with the container. Suitable containers include, for example, bottles, vials, syringes, etc. The containers may be formed from a variety of materials such as glass or plastic. A single container or multiple containers may hold (separately or together) the CCL2, or a biologically active fragment thereof, and (a) a long-acting progestin-only contraceptive, or (b) another agent that inhibits abnormal uterine bleeding, and may have a sterile access port (for example the container may be an intravenous solution bag or a vial having a stopper pierceable by a hypodermic injection needle or an aerosol spray device). The label or package insert indicates that the composition is used for treating the condition of the invention.

Alternatively, or additionally, the kit may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Materials and Methods

Tissues.

After receiving written informed consent at New York University under Institutional Review Board approval, paraffin sections were derived from banked paired endometrial tissues obtained before and after Depo therapy by Pipelle biopsy from each reproductive age woman with regular menstrual cycles during the secretory phase (n=6). Based on an established animal model for LAPC-induced AUB in humans (9), nulliparous adult female pigmented GPs (weighing 525-775 g) were used in experimental procedures conforming to National Health and Medical Research Council Guidelines of Australia and approved by the Animal Ethics Committee of The University of Western Australia. GPs (n=24) were subjected to bilateral OVX and given subcutaneous 21-d time-release pellets (Innovative Research of America) containing MPA (50 mg/d; n=6) or 17β-Estradiol ($E_2$) (0.1 mg/d; n=6), both MPA and $E_2$ (n=6), or no pellets (n=6). On day 20 of exposure to the pellets, GPs were killed with pentobarbital and uterine tissues fixed in 10% formalin and processed for paraffin embedding. In vitro experiments used aortic VSMCs from premenopausal women (n=2) (Life Technologies).

Immunohistochemistry.

Paraffin sections (5 μm) from paired pre- vs. post-Depo treated human or GP endometria were deparaffinized, boiled in citrate buffer (pH: 6.0) and then incubated in methanol containing 3% $H_2O_2$. Following 10% normal horse serum blocking (Vector Labs), slides were incubated overnight at 4° C. with mouse anti-PCNA monoclonal antibody (EMD Millipore). After several rinses in Tris-buffered saline containing 0.1% tween-20 (TBS-T; pH 7.6) slides were then incubated with biotinylated anti-mouse IgG (Vector Labs) for 30 min, then with a streptavidin-peroxidase complex (Elite ABC kit; Vector Labs) for 30 min and with diaminobenzidine (DAB; Vector Labs) for 3 min. These steps, unless otherwise specified, were repeated for double-immunolabeling using 10% normal goat serum, rabbit anti-αSMA polyclonal antibody for 1 h (Abcam), a goat biotinylated anti-rabbit IgG (Vector Labs), and a streptavidin-alkaline phosphatase (ABC kit) and Vector Red (Vector Labs). For negative controls, normal mouse IgG2a and rabbit IgG were used at the same concentrations as the primary antibodies. Slides were counterstained by Hematoxylin and evaluated by histological scoring (HSCORE), as described previously (34). (See details for HSCORE evaluation for αSMA immunoreactivity and PCNA quantitation in SI Materials and Methods).

Cell Cultures and Experimental Incubations.

VSMCs were thawed and cultured in medium 231 (M231; Life Technologies) with smooth muscle growth supplement (5% FBS; 2 ng/mL human basic fibroblast growth factor, 0.5 ng/mL human epidermal growth factor, 5 ng/mL heparin, 0.2 μg/mL insulin and 5 μg/mL BSA; Life Technologies) with 100 U/mL penicillin, 100 µg/mL streptomycin, 0.25 µg/mL fungizone. Confluent VSMCs were washed twice with 1×PBS to remove residual serum, passaged in 96-well or 6-well plates and incubated in parallel in M231 with 1% charcoal striped FBS with 0.1% ethanol (vehicle, control) or $10^{-7}$ M MPA (Sigma-Aldrich) or $10^{-7}$ M ETO (Organon) or $10^{-7}$ M $P_4$ (Sigma-Aldrich) for 15 min, 6, 48, and 72 h. VSMCs were then washed with ice-cold PBS and stored at −80° C. for further RNA and protein analyses.

Cell Proliferation and Apoptosis Assay.

VSMCs were grown in 96-well plates or 8-well chamber slides and incubated with $10^{-7}$ M of MPA (Sigma-Aldrich) or ETO (Organon) or $P_4$ (Sigma-Aldrich) or vehicle±rCCL2 (R&D Systems)±STAT1 inhibitor, 5′-methyl-thioadenosine (MTA; EMD Millipore) (19) for 48 or 72 h. VSMCs were then analyzed for apoptosis by an ELISA based apoptosis kit (Roche) or cleaved-caspase 3 immunostaining. VSMC proliferation was measured by BrdU incorporation Kit (Cell Signaling). (See further details in SI Materials and Methods).

Microarray Analysis.

Total RNA was isolated using Qiagen miRNeasy Mini Kit (Qiagen) and RNeasy MinElute Cleanup Kit (Qiagen). The quality of isolated RNAs was confirmed using an Agilent 2100 Bioanalyzer. Microarray analysis was limited to those specimens in which RNA Integrity Number exceeded 8. Microarray processes were performed in the Keck Biotechnology Resource Laboratory at Yale University (New Haven, Conn.) using Illumina Human HT-12 v4 BeadChip (Illumina). Raw data without normalization were analyzed by GeneSpring GX12.5 software (Agilent Technologies-Silicon Genetics). Normalization was performed as described (35). Genes with a fold-change >1.25 and a P value<0.05 were considered differentially expressed. Ingenuity Pathway Analysis (IPA) software (Qiagen) explored molecular and biological networks related to differentially expressed genes.

Western Blot Analysis.

To confirm inhibition of STAT1 signaling in LAPC-treated VSMCs, detected by IPA, cell lysates from VSMCs were run in 10% Tris-HCl gel (Bio-Rad). Transfer onto membrane, blocking, washing, chemiluminescence development, and stripping/reprobing were performed as described previously (35). The membrane was incubated with antitotal STAT1 or antiphospho-STAT1 rabbit monoclonal antibodies (Cell Signaling) and then with peroxidase-conjugated goat anti-rabbit IgG (Vector Labs). Signals were developed by a chemiluminescence kit (GE Healthcare).

qRT-PCR.

For qRT-PCR, 500 ng total RNA from each treatment was reverse transcribed by using RETROscript kit (Ambion). qRT-PCR was performed using the TaqMan Gene Expression Assay Kits for H19, TMEM119, RARRES1, and CCL2 (TaqMan ID # Hs00262142_g1, Hs01938722_m1, Hs00161204_m1 and Hs00234140_m1, respectively; Life Technologies) as described previously (36). Expression of the target mRNAs was normalized to β-actin levels, and the $2^{-\Delta\Delta CT}$ was used to calculate relative expression levels.

Transwell Insert Migration Assays.

VSMCs (75,000 cells/200 µL) were suspended in M231 containing 1% charcoal striped FBS and either 0.1% ethanol (vehicle control) or the corresponding steroids and seeded onto insert wells (transwell filter with 12-µm pores; EMD Millipore). The inserts were then placed in 24-well plates containing 500 µL M231 with 1% charcoal striped FBS. After 12 h, cells remaining on the upper surface of the filter were removed with a cotton swab. Migrated cells were trypsinized, centrifuged, and resuspended in 200 µL of M231 medium. The cell suspensions were mixed with 200 µL 10% ethanol containing 0.4% Trypan blue dye and the live cell number was counted by Countess Automated Cell Counter (Invitrogen). See further details in SI Materials and Methods.

Statistical Analysis.

HSCOREs were normally distributed with equal variance between comparison groups and compared by Student's t-test. Western blot or qRT-PCR results were normally distributed as determined by Kolmogorov-Smirnov test and analyzed by one-way ANOVA followed by testing post hoc Holm-Sidak method using SigmaStat v3.0 software (Systat Software). A P value<0.05 is accepted as statistically significant.

SI Materials and Methods

In Vitro VSMC Proliferation Assay by BrdU Incorporation.

VSMCs were thawed and cultured in T-75 cell culture flasks in medium 231 (M231; Life Technologies) with smooth muscle growth supplement (5% FBS; 2 ng/mL human basic fibroblast growth factor, 0.5 ng/mL human epidermal growth factor, 5 ng/mL heparin, 0.2 µg/mL insulin and 5 µg/mL BSA; Life Technologies) with 100 U/mL penicillin, 100 µg/mL streptomycin, and 0.25 µg/mL fungizone. Confluent VSMCs were washed twice with 1×PBS to remove residual serum, and then passaged (5,000 cells per well) in 96-well plates and incubated in parallel in M231 with 1% charcoal striped FBS with 0.1% ethanol (vehicle, control), $10^{-7}$ M MPA (Sigma-Aldrich), $10^{-7}$ M ETO (Organon), or $10^{-7}$ M $P_4$ (Sigma-Aldrich)±rCCL2 (monocyte chemotactic protein-1; R&D Systems)±STAT1 inhibitor, 5′-methyl-thioadenosine (MTA; EMD Millipore) for 48 or 72 h.

BrdU (Cell Signaling) 1× in 100-µL M231 was added to each well during the final 24 h of incubation. At the end of 48- or 72-h incubation period, medium was removed and the wells washed twice with ice-cold PBS. VSMC proliferation was measured using BrdU cell proliferation Kit (Cell Signaling) at room temperature. Cells was incubated in 100 µL per well of the fixing/denaturing solution for 30 min, and then replaced by 100 µL per well BrdU detection antibody solution for 1 h. Following three rinses with wash buffer, plates were incubated in HRP-conjugated secondary antibody (100 µL per well) for 30 min. After three additional rinses with wash buffer, tetramethylbenzidine substrate solution (100 µL per well) was added for 20 min and the reaction stopped by adding 100 µL per well STOP solution. Absorbance was measured at 450 nm using Spectra Max190 microplate reader (Molecular Devices) to detect BrdU incorporation in each well.

In Vitro VSMC Apoptosis Assay.

This assay detects late-stage apoptosis by quantifying specific mono- and oligonucleosomes in the cytoplasmic fraction of cell lysates using mouse monoclonal antibodies directed against DNA and histones. In late-stage apoptosis (following nuclear fragmentation), cell cytoplasm contains mono- and oligonucleosomes, absent in normal (nonapoptotic) cells. The nucleosomes contained in the sample bind via their histone component to the immobilized antihistone antibody. Anti-DNA peroxidase reacts with the DNA part in the nucleosome. After removal of unbound peroxidase conjugate, the amount of peroxidase retained in the immunocomplex is detected by measuring colorimetric reaction.

Apoptosis index was determined in a second set of experiments. VSMC cultures (10,000 cells per wells) were incubated in 96-well plates with the treatments described above. Briefly, at the end of 48- or 72-h incubation periods, cells were washed three times in ice-cold PBS and cell lysate prepared by incubating each well in 200-μL lysis buffer for 30 min, followed by centrifugation at 200×g for 10 min. Duplicate 20-μL supernatant of cytoplasmic fractions from each treatment were carefully pipetted into streptavidin-coated microplates. A 20-μL VSMC culture supernatant devoid of cell fractions was used as a negative control, and 1-, 5-, 10-, and 20-μL supernatants containing camptothecin-induced apoptotic cell fractions were used as positive controls (ELISA based cell death detection kit$^{plus}$, Roche Applied Science). Incubation buffer was used as background control (Roche Applied Science). Then, each well was brought to 100 μL by adding immunoreagent (peroxidase-conjugated anti-DNA complex) and incubated by gentle shaking (300 rpm) for 2 h. To develop colorimetric reaction, removal of the immunoreagent solution by tapping and rinsing each well three times with 300-μL incubation buffer was followed by incubation of each well with 100-μL substrate solution containing ABTS [2, 2'-azino-bis(3-ethylbenzothiazoline-6-sulphonic acid)] on a plate shaker at 250 rpm for 20 min. The immunoreaction was stopped with 100 μL ABTS Stop Solution and measured at 405 nm against 100 μL ABTS solution+100 μL ABTS stop solution as a blank (reference wavelength 490 nm) using Spectra Max190 microplate reader (Molecular Devices).

Cleaved Caspase-3 Immunocytochemistry and Detection of Nuclear Fragmentation.

VSMCs treated with control, $10^{-7}$ M MPA (Sigma-Aldrich), $10^{-7}$ M ETO (Organon), or $10^{-7}$ M $P_4$ (Sigma-Aldrich) in eight-well chamber slides (two sets) were fixed with 4% PFA, washed three times with PBS-T (PBS with 0.3% Triton X-100).

The first set of eight-well chamber slides was processed for cleaved caspase-3 immunocytochemistry. Slides were blocked with 3% $H_2O_2$ and then with 5% normal goat serum prepared in PBS-T (Vector Labs) for 60 min. Following aspiration of the blocking solution, cells were incubated overnight at 4° C. with rabbit anticleaved caspase-3 (Cell Signaling). After rinsing three times in PBS, slides were incubated with goat biotinylated anti-rabbit secondary antibody (diluted 1/400) and then washed followed incubation with streptavidin-biotin complex (Vector Labs) for 30 min at room temperature. After several rinses, immunoreaction was developed by incubation with DAB (Vector Labs) for 3 min and followed by slight counterstaining in Hematoxylin for 30 s and mounted with permanent Clear-Mount solution (EMS). Cleaved caspase-3 immunoreactivity in groups was then evaluated as described for αSMA in the HSOCRE section.

The second set of VSCMs in eight-well chamber slides was stained with FITC-conjugated phalloidin (Sigma-Aldrich) for 60 min. After washing with 5 PBS, cells were then treated with DAPI (Sigma-Aldrich) for 15 min, washed again, and mounted with antifade mounting medium (Vector Labs). In each treatment condition, the nuclear fragmentations in VSMCs were counted in five different areas in the slides and mean nuclear fragmentation value were detected using Observer Z.1 fluorescence microscope and ZEN image analyzer software (Carl Zeiss).

Transwell Insert Migration Assays.

Cultured VSMCs were grown in T-75 cell culture flasks in M231 (Life Technologies) with smooth muscle growth supplement (Life Technologies) with 100 U/mL penicillin, 100 μg/mL streptomycin, 0.25 μg/mL fungizone. Confluent VSMCs were washed twice with 1×PBS to remove residual serum, and then trypsinized, resuspended (75,000 cells per 200 μL per well) in M231 with 1% charcoal striped FBS with 0.1% ethanol (vehicle, control), $10^{-7}$ M MPA (Sigma-Aldrich), $10^{-7}$ M ETO (Organon), or $10^{-7}$ M $P_4$ (Sigma-Aldrich)±rCCL2 (R&D Systems) and seeded on insert wells (transwell filter with 12-μm pores; EMD Millipore), which were then placed in 24-well plates containing 500 μL M231 with 1% charcoal striped FBS. After 12 h, cells remaining on the upper surface of the filter were removed with a cotton swab. Migrated cells attached to the lower surface of each insert or to the surface of lower wells were collected by trypsinization, followed by centrifugation and resuspension in 200 μL of M231 medium. The cell suspensions were mixed with 200 μL 10% ethanol containing 0.4% Trypan blue dye (selectively stains only dead cells blue, whereas live cells with intact cell membranes remain unstained) for 5 min. A mixture of 100 μL M231 and 100 μL 10% ethanol containing 0.4% Trypan blue dye was used as a negative control. To detect live cell numbers, 10 μL of final cell/Trypan blue dye suspension from each treatment condition was pipetted into Countess Cell Counting Chamber Slide and counted by using Countess Automated Cell Counter (Invitrogen). The counting procedure was performed in duplicate.

HSCORE Analysis of α-SMA and Quantitation of PCNA Immunoreactivity.

Staining intensity for α-SMA was semiquantitatively evaluated by Q:1 HSCORE (1). Specifically, staining intensity was classified among the following categories: 0 (no staining), 1 (weak), 2 (moderate), and 3 (intense). An HSCORE value was determined for each specimen by using the formula HSCORE=$\Sigma P_i$ (i+1), where $P_i$ is the percentage of stained cells in each intensity category (i.e., i=1, 2, or 3).

Quantitation of PCNA immunostaining was determined by counting the number of PCNA$^+$ (brown) and PCNA$^-$ cell nuclei (blue) in VSMCs (αSMA immunostained cells) and obtaining the ratio of numbers of PCNA$^+$ cell nuclei to total αSMA$^+$ cells. For each slide, three different fields were evaluated microscopically at 200× magnification. Slides were evaluated at different times by two investigators blinded to tissue source, and the average HSCORE or percentage of cells with PCNA$^+$ nuclei to total αSMA$^+$ cells used.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Decreased Endometrial VSMC Proliferation in Women Receiving Depo

Figure 9A:
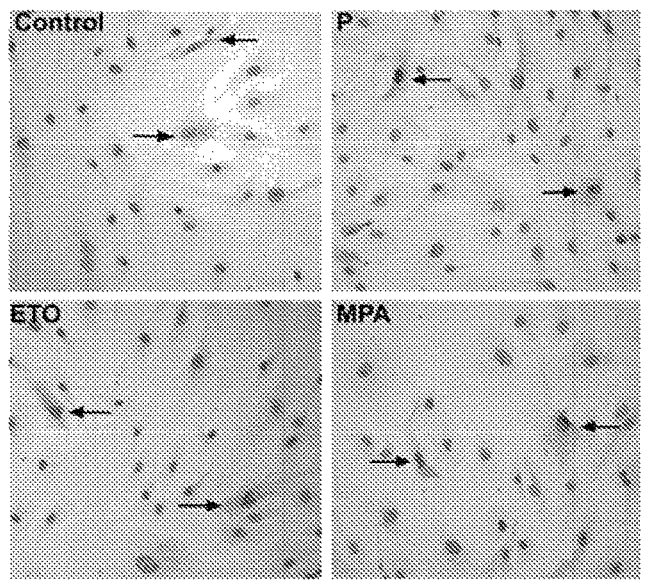
Figures 1, 9A:
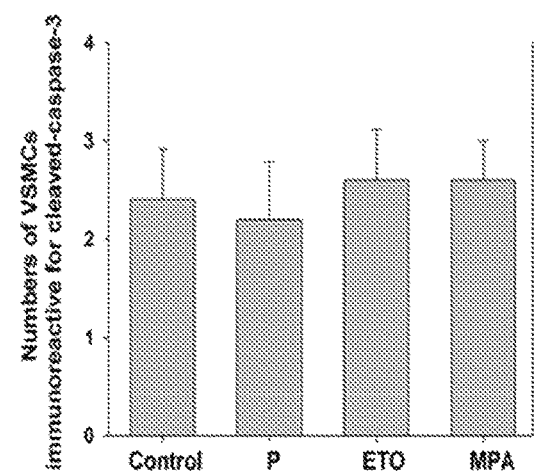
Figure 9B:
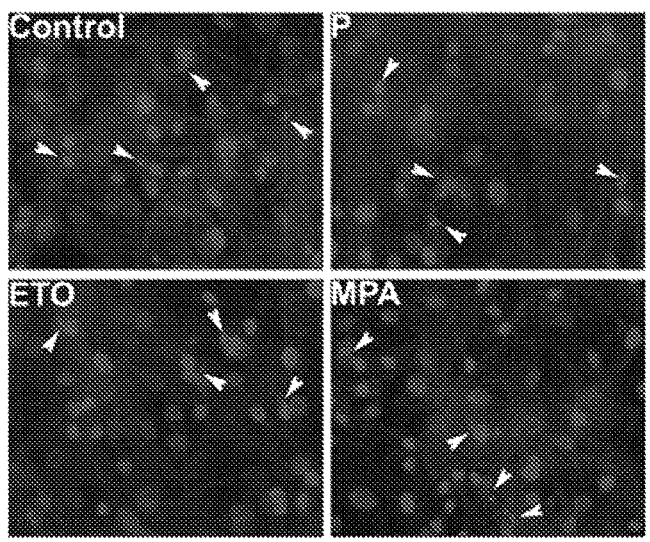
Figures 1, 9B:
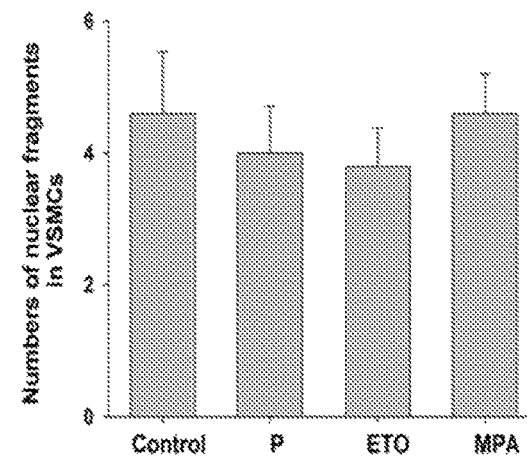

VSMC numbers and proliferation index were evaluated in microvessels and spiral arteries of paired endometrial sections from women before and after Depo (injectable MPA) after double-immunostaining for αSMA and proliferating cell nuclear antigen (PCNA). Staining intensity and numbers of αSMA+ cells around microvessels (FIG. 1A vs. 1B) and spiral arteries (FIG. 1C vs. 1D) were lower in pre- vs. post-Depo-treated endometria (mean±SEM: 117.8±14.4 vs.

205.8±22.0, respectively; P<0.008) (FIG. 1E). The VSMC proliferation index was significantly lower in post-(FIGS. 1A and 1C) vs. pre-Depo endometria (FIGS. 1B and 1D) (24.7%±3.5 vs. 57.8%±6.9; P<0.003) (FIG. 1F).

Example 2—LAPC-Regulated Genes are Involved in VSMC Differentiation and Proliferation Microarray analysis revealed that MPA and ETO altered transcription of 793 and 191 genes, respectively, in cultured VSMCs, whereas progesterone ($P_4$) modified only 40 genes. (See complete microarray results at www.ncbi.nlm.nih.gov/geo/query/acc.cgi?acc=GSE55736 in the Gene Expression Omnibus repository using access no. GSE55736). Of 793 genes differentially regulated by MPA, 392 are up-regulated and 401 are down-regulated. Of 191 genes differentially regulated by ETO, 82 are up-regulated and 109 are down-regulated. Of 40 genes differentially regulated by $P_4$, 18 are up-regulated and 22 are down-regulated. Tables 2-4 display the 40 most progestin-regulated genes. The Venn diagram displaying microarray data revealed that 612 genes are regulated solely by MPA, 13 solely by ETO, 16 solely by $P_4$, and 15 genes by all three progestin (FIG. 2A). Of ETO-modulated genes, 92% (175) are also regulated by MPA (FIGS. 2B-2E) with the same directional change [i.e., MPA and ETO induce transmembrane protein 119 (TMEM119), a suppressor of myoblast differentiation, and suppress retinoic acid receptor responder (tazarotene induced) 1 (RARRES1), a proliferation inducer] (Tables 2 and 3).

Figure 3A:
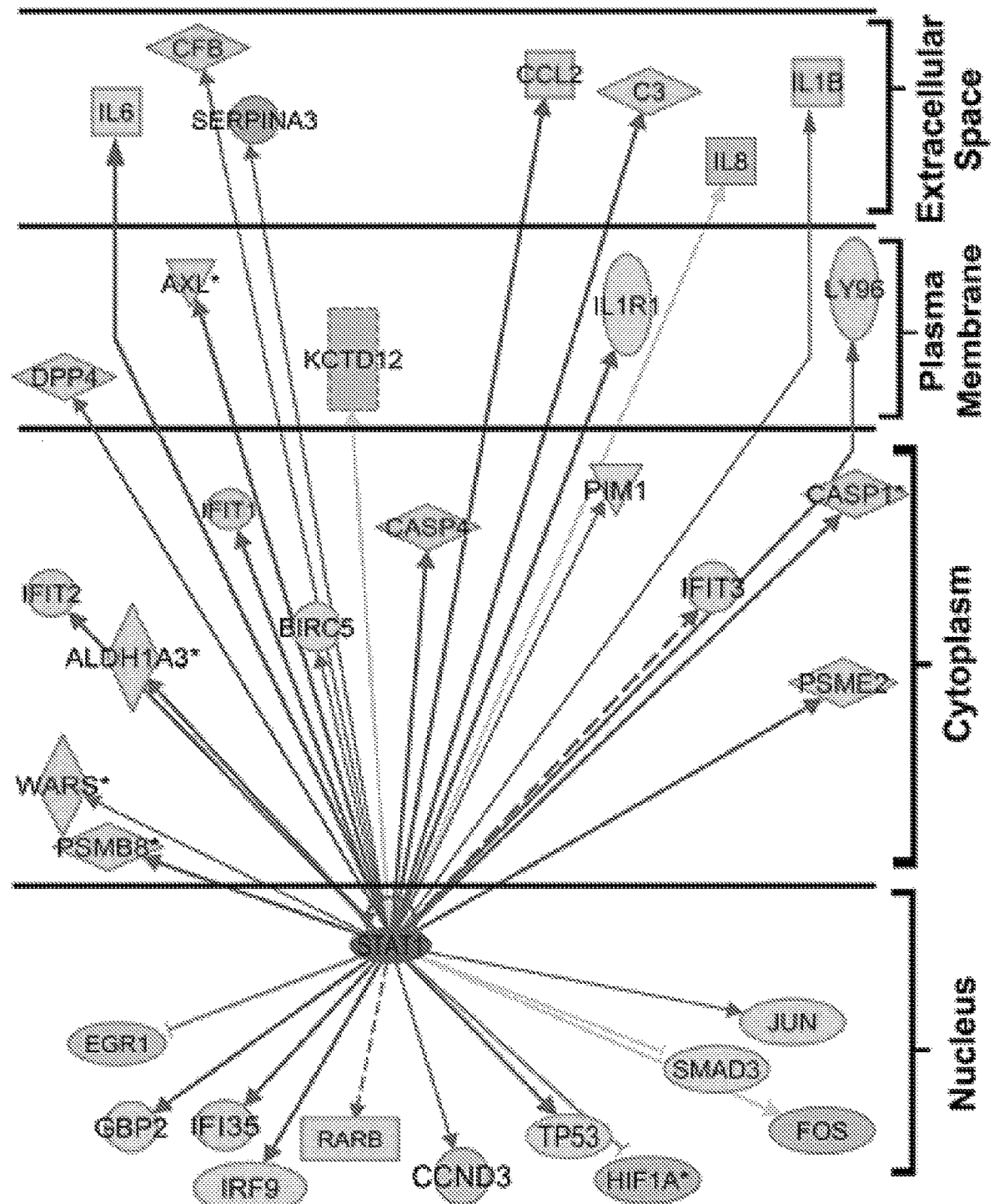
Figure 3A:
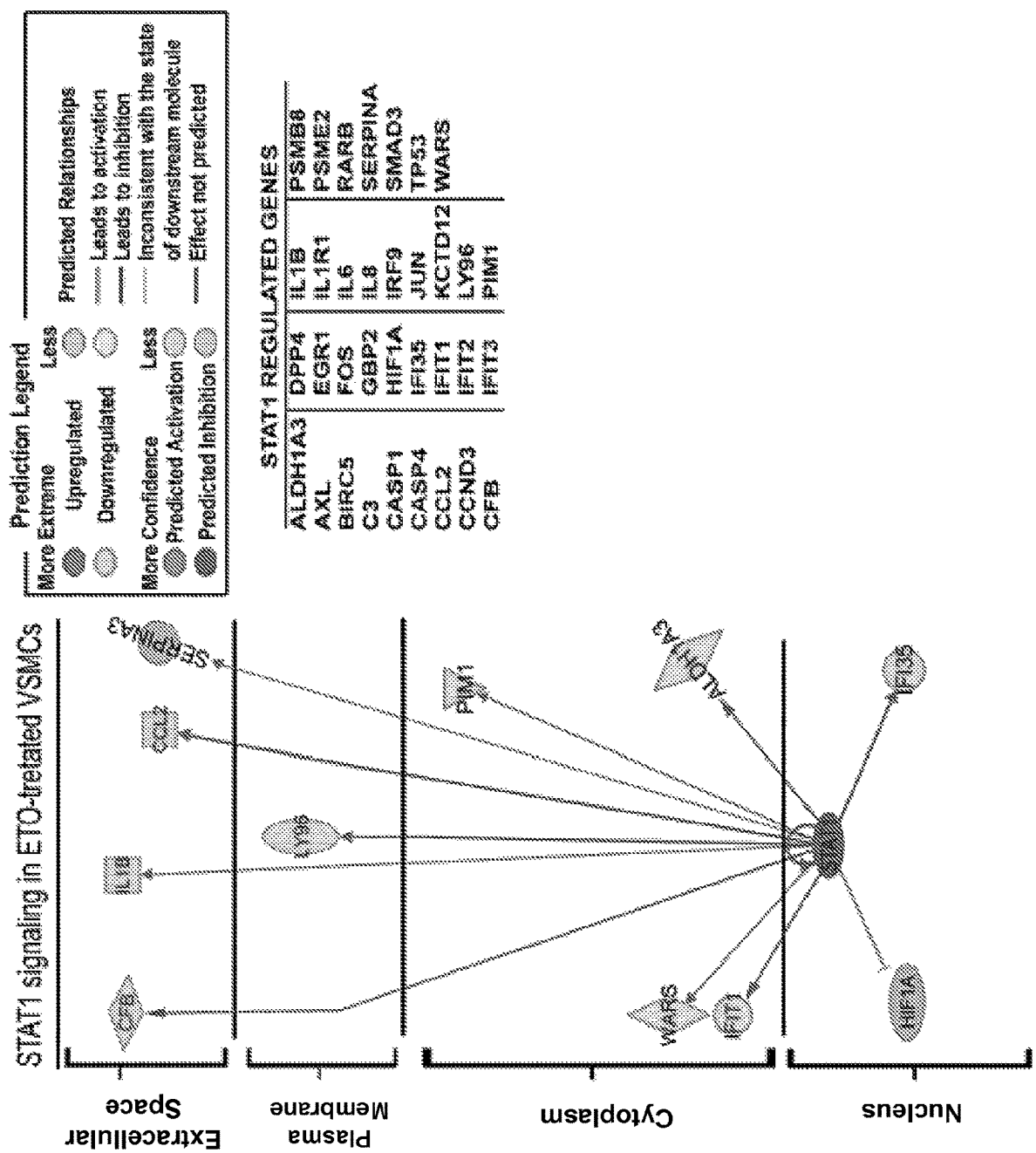

Among MPA- and ETO-regulated genes, H19 imprinted maternally expressed transcript, noncoding RNA (H19), TMEM119, RARRES1, and chemokine (C-C motif) ligand 2 (CCL2) mediate differentiation, proliferation, and migration of VSMCs (15-18) and were thus chosen for quantitative RT-PCR (qRT-PCR) confirmation. In parallel with the microarray results (Tables 2 and 3), WA or ETO up-regulated H19 mRNA and TMEM119 mRNA, and down-regulated RARRES1 mRNA and CCL2 mRNA levels (FIGS. 2B-2E). Further evaluation of microarray data by Ingenuity Pathway Analysis (IPA) software predicts that STAT1 inhibition is associated with genes regulated in VSMCs by WA or ETO (z-score and the overlap P value; −3.06, P<8.5×10$^{14}$ and −2.43, P<2.2×10$^{-6}$, respectively) (FIG. 3A). Confirming this prediction, compared with control VSMCs, Western blotting found that WA and ETO partially reduced phosphorylated levels of STAT 1 but not total STAT1 levels (FIG. 3B).

Whole genome microarray analysis revealed that compared with vehicle (control), WA or ETO treatment altered transcription of 793 and 191 genes, respectively in cultured VSMCs, whereas $P_4$ treatment modified transcription of only 40 genes. Specifically, of the 793 differentially regulated genes in the MPA-treated VSMCs, 392 genes (49%) are up-regulated and 401 (51%) are down-regulated. Of the 191 differentially regulated genes in the ETO-treated VSMCs, 82 (43%) are up-regulated, 109 (57%) are down-regulated. Of the 40 differentially regulated genes in the P4-treated VSMCs, 18 (45%) are up-regulated, 22 (55%) are down-regulated (Table 1).

612 genes are regulated solely by MPA and 13 genes are regulated solely by ETO, whereas 16 genes are regulated solely by $P_4$. In contrast, 15 genes are regulated in common by all three progestins. Among ETO-regulated genes, 92% (175 genes) are also regulated by MPA at the same directional change (FIG. 2A).

TABLE 1

| | Up-related genes | Down-regulated genes | Total regulated genes |
| --- | --- | --- | --- |
| MPA | 392 | 401 | 793 |
| ETO | 82 | 109 | 191 |
| P4 | 18 | 22 | 40 |

Figure 4A:
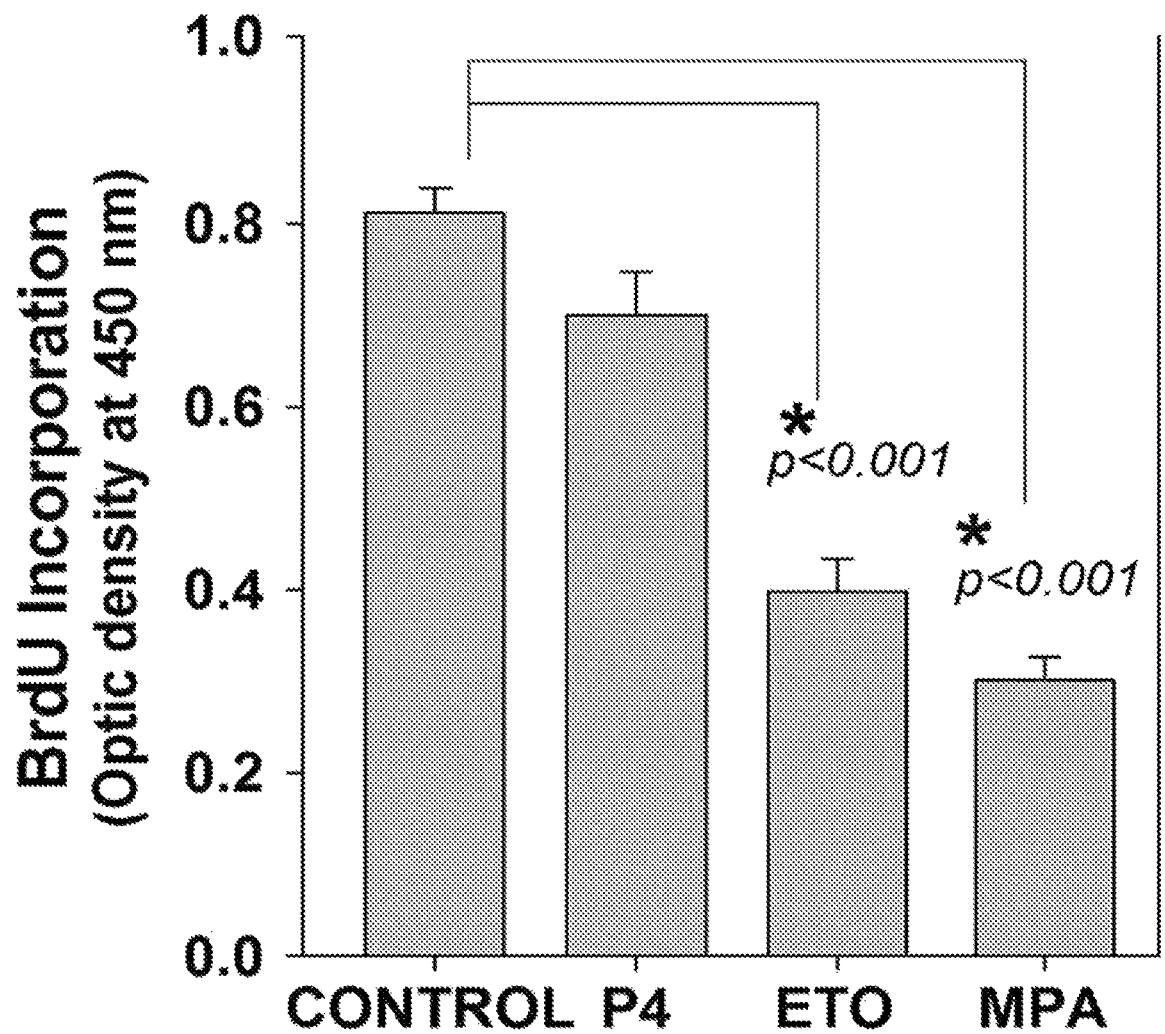
FIGS. 4A-4C. LAPCs inhibit VSMC proliferation. BrdU incorporation (FIG. 4A) or apoptotic index (FIG. 4B) in VSMCs treated with control (vehicle), $10^{-7}$ M $P_4$, $10^{-7}$ M ETO, or $10^{-7}$ M MPA for 48 h. BrdU incorporation in VSMCs treated with control (vehicle), 1 or 10 ng/mL CCL2 or $10^{-7}$ M $P_4$ or $10^{-7}$ M ETO or $10^{-7}$ M MPA±CCL2 (10 ng)±100 μM MTA (Stat1 inhibitor) for 72 h (FIG. 4C). Bars represent mean±SEM, n=3 with four replicates per experiment.
Figure 4B:
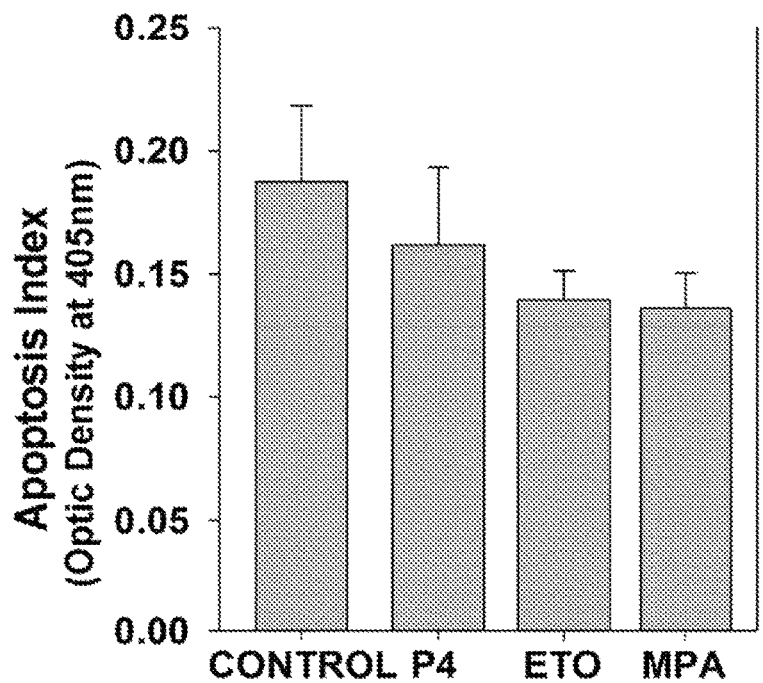
Figure 4C:
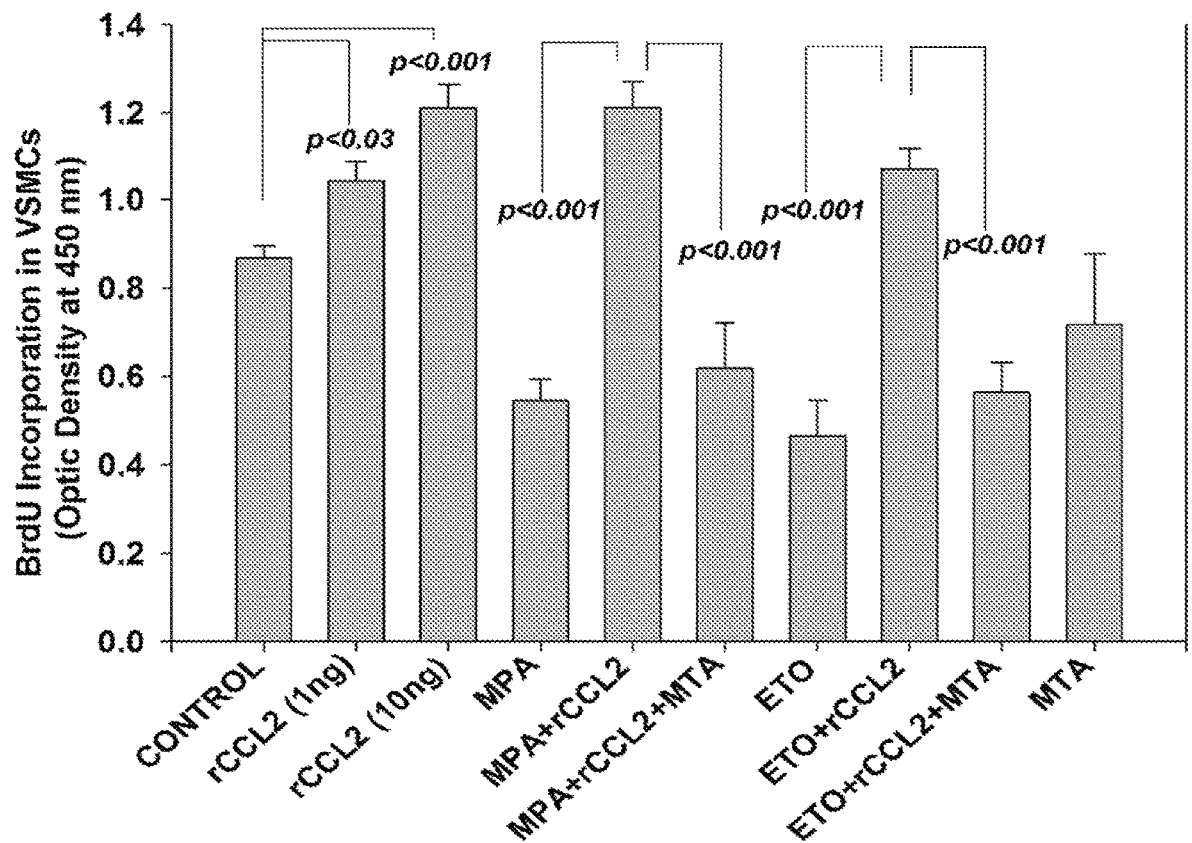

Example 3—LAPC Inhibition of VSMC Proliferation is Reversed by CCL2 Via STAT1 Signaling In cultured VSMCs, 48-h treatment with MPA or ETO significantly reduced BrdU incorporation vs. control (mean±SEM 0.31±0.02 or 0.40±0.03 vs. 0.81±0.03 respectively; P<0.001), whereas P4 (0.71±0.05) was ineffective (FIG. 4A). In contrast, in parallel experiments, none of the progestins altered apoptosis (FIGS. 9A-1, 9A-2, 9B-1, 9B-2). To determine if inhibition of VSMC proliferation by MPA or ETO is mediated by decreased CCL2 expression, VSMCs were treated with vehicle or MPA or ETO±recombinant CCL2 (rCCL2) for 7 h. Compared with control (0.86±0.03), rCCL2 elicited a concentration dependent increase in BrdU incorporation (1.05±0.05 and 1.21±0.05, respectively; P<0.005) (FIG. 4C). Addition of 10 ng/mL rCCL2 reversed the inhibitory effects of MPA or ETO, whereas 100 μm MTA, a specific STAT1 inhibitor (19), abolished these rCCL2 effects (FIG. 4C).

Example 4—LAPCs Inhibit VSMC Migration In Vitro

Figure 5:
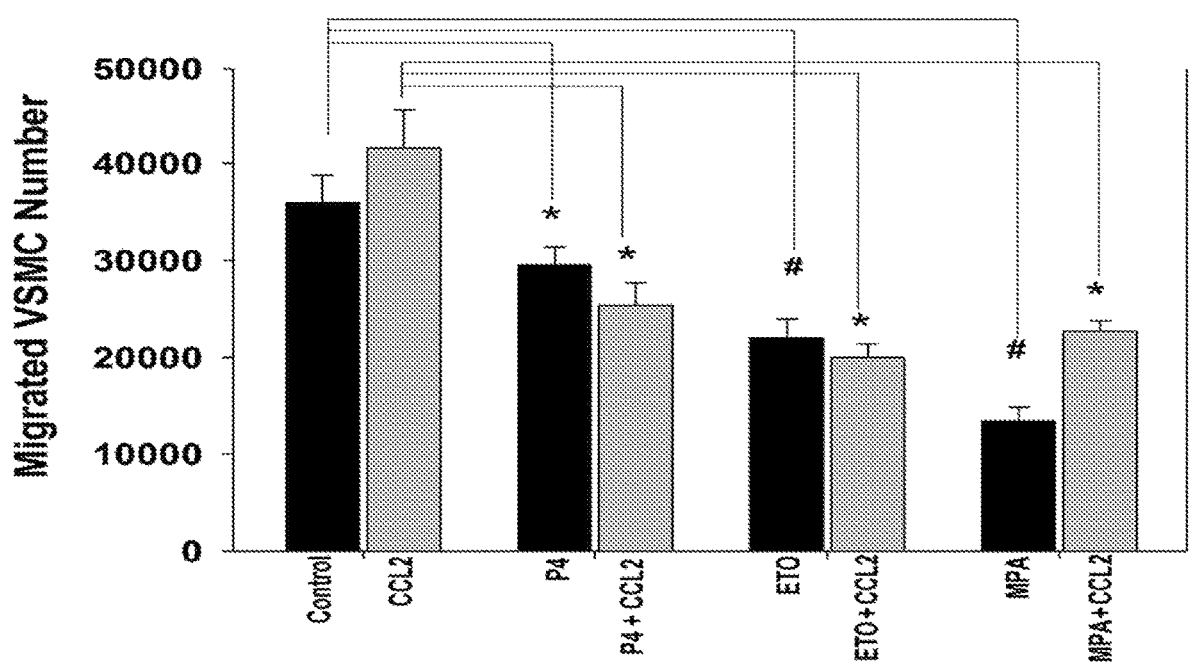
FIG. 5. LAPCs reduces VSMC migration. VSMCs treated with vehicle (control) or $P_4$ or ETO or MPA in the presence or absence of 10 ng/mL rCCL2 seeded on insert transwell membranes and allowed to migrate to lower wells for 12 h. Bars represent mean±SEM, n=3 with three replicates in each independent experiments; *P<0.05 and # P<0.001.

Compared with control (migration rate: 48.4%), 12-h incubation with MPA or ETO or $P_4$ reduced migration of VSMCs (migration rate: 18.7% or 29.6% or 39.4%, respectively; P<0.001) (FIG. 5). In coincubations, rCCL2 did not reverse inhibition of VSMC migration by ETO or $P_4$, but partially reversed the MPA effect (FIG. 5).

Figure 6A:
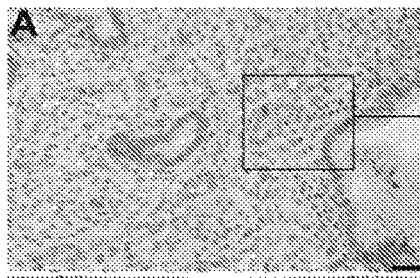
FIGS. 6A-6H. Endometria of OVX-GPs treated by MPA display reduced αSMA and PCNA immunoreactivity in VSMC. In double-immunostained sections, immunoreactivity for αSMA (red) and PCNA (brown) in VSMCs surrounding vessels throughout the endometrium of OVX-GPs treated with vehicle (FIGS. 6A and 6B), $E_2$ (FIGS. 6C and 6D), $E_2$+MPA (FIGS. 6E and 6F), or MPA (FIGS. 6G and 6H) for 21 d. Starts indicate vessel lumens. Note that discontinuous αSMA immunoreactivity in OVX-GPs (FIG. 6B) becomes continuous and increases by the $E_2$ administration (FIG. 6D), whereas immunoreactive αSMA disappears in superficial endometrial vessels by $E_2$+MPA (FIG. 6F) or MPA (FIG. 6H) administration. Greater numbers of PCNA (+) nuclei (brown) among VSMCs (red) are present in endometrium from GPs following $E_2$ administration compared with vehicle control (FIGS. 6A and 6B), $E_2$+MPA (FIGS. 6E and 6F), or MPA (FIGS. 6G and 6H) administration. (Scale bars, 40 μm).
Figure 6B:
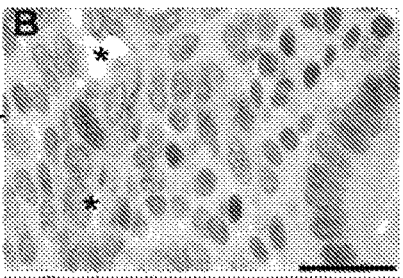
Figure 6C:
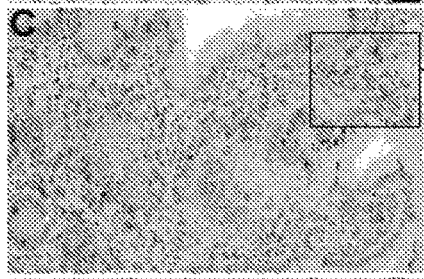
Figure 6D:
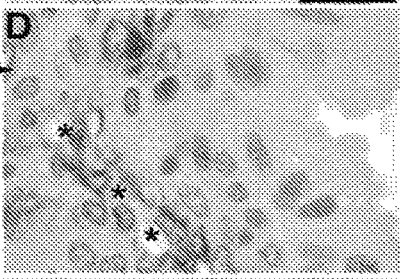
Figure 6E:
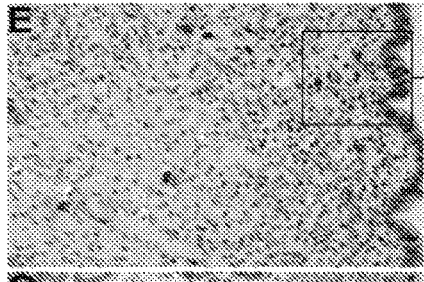
Figure 6F:
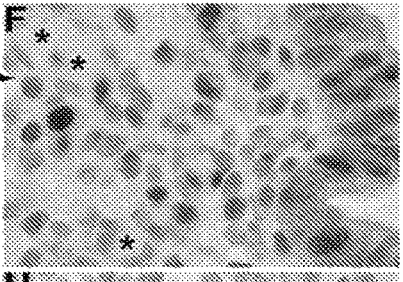
Figure 6G:
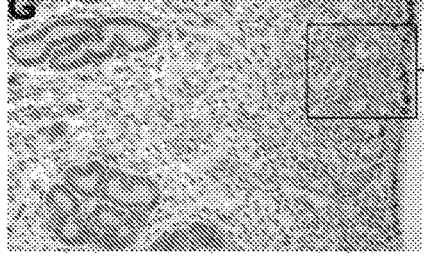
Figure 6H:
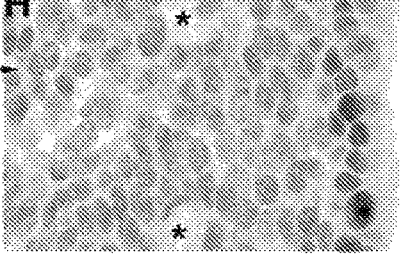

Example 5—MPA Administration Decreases Endometrial VSMC Numbers in Oophorectomized GPs Endometrial sections from control, $E_2$, $E_2$+MPA, or MPA-treated oophorectomized (OVX) GPs were double-immunostained for αSMA and PCNA. Controls displayed moderate to weak discontinuous αSMA immunoreactivity in vessels across the endometrium (FIGS. 6A and 6B). In comparison, $E_2$-administered GPs displayed elevated numbers of αSMA immunoreactive VSMCs with intense and continuous immunostaining across the endometrium (FIGS. 6C and 6D). Addition of MPA blunted these $E_2$ effects and resulted in discontinuous αSMA immunostaining along vessels in the basal layer (FIG. 6C vs. 6E) and absence of immunoreactive cells around superficial layer vessels (FIG. 6F). Similarly, αSMA immunoreactivity was weaker (FIG. 6A vs. 6G) and virtually absent around superficial endometrial vessels in GPs administered MPA alone vs. control (FIG. 6B vs. 6H). Semiquantitative evaluation revealed that $E_2$ elicited higher αSMA histological scoring (HSCOREs) vs. control (mean±SEM; 212.7±14.6 vs. 135.2±26.0, P<0.005) (FIG. 7A), whereas $E_2$+MPA significantly lowered αSMA HSCOREs vs. $E_2$ alone (116.7±13.84 vs. 212.7±14.6, respectively; P<0.005) (FIG. 7A). Similar effects were observed following administration of MPA alone vs. $E_2$ alone (83.50±9.0 vs. 212.7±14.6, respectively;

P<0.001) (FIG. 7A). In double-stained sections, PCNA+ endometrial VSMC numbers are significantly higher in the $E_2$ vs. control group (mean±SEM; 36.8%±2.7 vs. 11.2%±2.3; P<0.001) (FIGS. 6A vs. 6C or 6B vs. 6D and 7B). Administration of $E_2$+MPA blocked $E_2$-enhanced endometrial VSMC proliferation (11.3%±2.5 vs. 36.8%±2.7, respectively; P<0.001) (FIGS. 6C vs. 6E or 6D vs. 6F and 7B). Administration of MPA alone vs. $E_2$ produced similar effects (10.2%±2.8 vs. 36.8%±2.7, respectively; P<0.001) (FIGS. 6C vs. 6G or 6E vs. 6H and 7B).

The endometria of women receiving LAPCs display irregularly distributed hyperdilated thin-walled vessels with deficient basement membranes that are the site of AUB (14, 20). This study reveals a novel mechanism that accounts for the development of this abnormal vasculature. Integration of in vitro findings in human VSMCs with in situ observations in MPA treated OVXGPs and in post-Depo (injectable form of MPA)-treated human endometria demonstrated the inhibitory role of the progestin component of LAPCs on VSMC proliferation and migration. This accounts for the hyperdilated microvessels in the superficial endometrium, which are devoid of normal VSMC layer and exhibit increased susceptibility to bleeding.

Previous studies investigated VSMC characteristics in the endometrium of normal cycling and LAPC-treated women (21-23). As an early differentiation marker, αSMA is expressed by VSMC of endometrial vessels, by pericytes attached to capillaries, and by stromal myofibroblasts (21, 22). Increased αSMA expression during the secretory phase (22) suggests a correlation between endometrial vascular maturation with αSMA expression. In support of this thesis, the VSMC proliferation index (24) and the number of endometrial vessels enveloped by more than one VSMC layer increases from the proliferative to secretory phase (25). Moreover, αSMA expression is decreased around endometrial microvasculature of Norplant users exhibiting bleeding (23). Building upon these prior reports, PCNA and αSMA double-immunolabeling now reveals a significant decrease in endometrial VSMC proliferation index, accounting for the reduction in VSMC numbers, reduced vascular wall thickness, and impaired structural integrity responsible for the hyperdilated thin-walled endometrial vessels seen in women receiving Depo. These pathological changes are consistent with lower VSMC proliferation in menorrhagic vs. normal endometrium (24). In mice, vascular leakage and bleeding from enlarged, thin-walled capillaries results from pericyte depletion caused by knockout of PDGF subunit B or PDGF receptor β genes (26, 27), indicating the crucial role played by pericyte/VSMCs in maintaining vascular integrity.

Given the lack of availability human endometrial VSMCs, progesterone receptor-expressing VSMCs isolated from human female aortas were used (28). The inventors' results revealed both common and unique responses of VSMCs to $P_4$, ETO, and MPA. Strikingly, much greater numbers of genes modulated by MPA compared with ETO or $P_4$ were found. This strong impact of MPA on gene regulation likely accounts for its greater local and systemic effects. However, the inventors focused on common genes regulated by ETO and MPA because AUB is a common side-effect seen in most LAPC users. Thus, the inventors confirmed mRNA levels of H19 (15), TMEM119 (17), RARRES1 (18), and CCL2 (16) because these genes are known to mediate VSMC differentiation, proliferation, and migration.

The present study demonstrates in situ inhibition of endometrial VSMC proliferation in post-Depo users, and in VSMC monolayers treated with MPA or ETO. This inhibition occurs in parallel with down-regulation of CCL2 by both progestins. Conversely, induction of VSMC proliferation by CCL2 (16, 29) suggests that this cytokine could act as an adjuvant treatment to reverse LAPC inhibition of VSMC proliferation. This strategy is supported by the current finding that rCCL2 reverses MPA and ETO mediated inhibition of VSMC proliferation in vitro.

Results of IPA and immunoblotting demonstrated that MPA and ETO-suppressed STAT1 signaling mediates inhibition of VSMC proliferation. In support of this mechanism, the STAT1 inhibitor, MTA, abolishes proliferative effects of CCL2 on untreated and progestin-treated VSMCs. These observations are consistent with reports that: (i) the CCL2 receptor CCR2 is present in human and rat VSMCs (30, 31), (ii) STAT1 signaling induces VSMC proliferation (32), and (iii) CCR2 activates STAT1 signaling (33).

Compared with other rodents, GPs share multiple reproductive tract anatomic and physiologic characteristics with humans (6, 7). Previous studies (8, 9) demonstrated that, as in human endometria, LAPC administration to GPs results in such endometrial vascular changes as focal hemorrhage, increased oxidative stress, high apoptotic indices, and elevated lipid peroxidation. Similarly, as in endometria of women receiving Depo, the present study confirmed reduced numbers of αSMA (+) cells and decreased VSMC proliferation in MPA-treated GP endometria, and confirms that in GPs treated with MPA, the majority of superficial endometrial vessels are devoid of VSMCs.

Although decreased proliferation and migration or increased apoptosis may contribute to the decreased density of the VSMC observed in the superficial endometria of LAPC users, the inventors show that apoptosis is unlikely to contribute to this abnormal vasculature because the apoptotic index was unaffected by WA or ETO or $P_4$. The partial reversal of MPA but not ETO or $P_4$ effects on VSMC migration by rCCL2 is likely a consequence of the mixed progestin-glucocorticoid properties of MPA vs. ETO, a purer progestin, or $P_4$. Alternatively, the greater number of genes regulated by MPA compared with ETO or $P_4$ may mediate this partial reversal.

These results reveal that LAPCs induce AUB by unique molecular and cellular mechanisms that impair endometrial VSMC proliferation, migration, or differentiation, and thus produce insufficient VSMCs to maintain vascular integrity. This novel process accounts for emergence of the thin-walled hyperdilated fragile vessels and focal hemorrhage seen in the endometria of LACP users (FIG. 8). These results also suggest that co-administration of CCL2 may reduce, prevent, or delay onset of LAPC-induced AUB.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 2

Forty most highly differentially regulated genes in VSMCs treated by MPA according to whole genome microarray analysis using Illumina HumanHT-12 v4 expression BeadChip kit.

| Gene name (symbol) | Fold-change | Location |
| --- | --- | --- |
| 1. H19 imprinted maternally expressed transcript, noncoding RNA (H19) | 5.440612 | Cytoplasm |
| 2. Leptin (obesity homolog, mouse) (LEP) | 4.041697 | Extracellular space |
| 3. Cysteine-rich secretory protein LCCL domain containing 2 (CRISPLD2) | 3.720673 | Cytoplasm |
| 4. Matrix Gla protein, transcript variant 1 (MGP) | 3.615251 | Extracellular space |
| 5. Matrix Gla protein, transcript variant 2 (MGP) | 3.220778 | Extracellular space |
| 6. Sushi domain containing 2 (SUSD2) | 2.901221 | Extracellular space |
| 7. Glutathione peroxidase 3 (plasma) (GPX3) | 2.827327 | Extracellular space |
| 8. Complement factor D (adipsin) (CFD) | 2.79403 | Extracellular space |
| 9. Actin, γ 2, smooth muscle, enteric (ACTG2) | 2.760889 | Cytoplasm |
| 10. Fibrillin 2 (FBN2) | 2.64234 | Extracellular space |
| 11. Collagen, type VIII, α 1, transcript variant 2 (COL8A1) | 2.627559 | Extracellular space |
| 12. Decorin, transcript variant A2 (DiCN) | 2.515078 | Extracellular space |
| 13. Alcohol dehydrogenase 1A (class I), α polypeptide (ADH1A) | 2.489634 | Cytoplasm |
| 14. Collagen, type VIII, alpha 1, transcript variant 2 (COL8A1) | 2.438741 | Extracellular space |
| 15. Prostaglandin-endoperoxide synthase 1 transcript variant 2, (PTGS1) | 2.437035 | Cytoplasm |
| 16. Insulin-like growth factor binding protein 2, 36 kDa (IGFBP2) | 2.366538 | Extracellular space |
| 17. EF-hand domain family, member D1 (EFHD1) | 2.294219 | Cytoplasm |
| 18. Transmembrane protein 119 (TMEM119) | 2.257849 | Cytoplasm |
| 19. Wingless-type MMTV integration site family, member 5A (WNT5A) | 2.218411 | Extracellular space |
| 20. Indolethylamine N-methyltransferase (INMT) | 2.18699 | Cytoplasm |
| 21. Chemokine (C-C motif) ligand 2 (CCL2) | −4.122792 | Extracellular space |
| 22. Retinoic acid receptor responder (tazarotene induced) 1, transcript variant 1, (RARRES1) | −4.060568 | Plasma membrane |
| 23. Complement factor B (CFB) | −3.169582 | Extracellular space |
| 24. Retinoic acid receptor responder (tazarotene induced) 1, transcript variant 2, (RARRES1) | −2.9936886 | Plasma membrane |
| 25. Latexin (LXN) | −2.9385219 | Cytoplasm |
| 26. PREDICTED: similar to LYPDC1 protein (LOC100134073) | −2.4009967 | Plasma membrane |
| 27. Natriuretic peptide precursor B (NPPB) | −2.3711812 | Extracellular space |
| 28. Hypothetical protein FLJ40504 (FLJ40504) | −2.3308704 | Unknown |
| 29. Interleukin 1, β (IL1B) | −2.3254209 | Extracellular space |
| 30. Filaggrin (FLG) | −2.3059754 | Cytoplasm |
| 31. LY6/PLAUR domain containing 1 transcript variant 1 (LYPD1) | −2.2100334 | Plasma membrane |
| 32. PREDICTED: keratin 18 pseudogene 13 (KRT18P13) | −2.209496 | Unknown |
| 33. Superoxide dismutase 2, mitochondrial transcript variant 2 (SOD2) | −2.2076235 | Cytoplasm |
| 34. Collectin subfamily member 12 (COLEC12) | −2.1771472 | Plasma membrane |
| 35. Pleckstrin homology-like domain, family A, member 1 (PHLDA1) | −2.1698341 | Cytoplasm |
| 36. DNA-damage regulated autophagy modulator 1 (DRAM1) | −2.1492844 | Cytoplasm |
| 37. Potassium voltage-gated channel, shaker-related subfamily, 0 member 1 transcript variant 2 (KCNAB1) | −2.0550146 | Plasma membrane |
| 38. ABI gene family, member 3 (NESH) binding protein (ABI3BP) | −2.0447865 | Extracellular space |
| 39. Bradykinin receptor B1 (BDKRB1) | −2.0408425 | Plasma membrane |

TABLE 2-continued

Forty most highly differentially regulated genes in VSMCs treated by MPA according to whole genome microarray analysis using Illumina HumanHT-12 v4 expression BeadChip kit.

| Gene name (symbol) | Fold-change | Location |
| --- | --- | --- |
| 40. UDP-N-acetyl-alpha-D-galactosamine:polypeptide N-acetylgalactosaminyltransferase 12 (GALNT12) | −1.9997492 | Cytoplasm |

TABLE 3

Forty most highly differentially regulated genes in VSMCs treated by ETO according to whole genome microarray analysis using Illumina HumanHT-12 v4 expression BeadChip kit.

| Gene name (symbol) | Fold-change | Location |
| --- | --- | --- |
| 1. H19, imprinted maternally expressed transcript noncoding RNA (H19) | 2.497379 | Cytoplasm |
| 2. Decorin, transcript variant A2, (DCN) | 1.761649 | Extracellular space |
| 3. Cysteine-rich secretory protein LCCL domain containing 2, (CRISPLD2) | 1.660543 | Cytoplasm |
| 4. Intelectin 2 (ITLN2) | 1.65464 | Extracellular space |
| 5. Leptin (obesity homolog, mouse) (LEP) | 1.601976 | Extracellular space |
| 6. Matrix Gla protein (MGP) | 1.581053 | Extracellular space |
| 7. Prostaglandin-endoperoxide synthase 1, transcript variant 2 (PTGS1) | 1.554942 | Cytoplasm |
| 8. Matrix Gla protein (MGP) | 1.55361 | Extracellular space |
| 9. RAB11 family interacting protein 1 (class I), transcript variant 3, (RAB11FIP1) | 1.550163 | Cytoplasm |
| 10. Alcohol dehydrogenase 1A (class I), alpha polypeptide (ADH1A) | 1.539702 | Cytoplasm |
| 11. cDNA FLJ20769 fis, clone COL06674 (PREDICTED: Receptor tyrosine kinase-like orphan receptor 1) | 1.528458 | Plasma membrane |
| 12. Actin, γ 2, smooth muscle, enteric (ACTG2) | 1.513948 | Cytoplasm |
| 13. Wingless-type MMTV integration site family, member 5A (WNT5A) | 1.504411 | Extracellular space |
| 14. EF-hand domain family, member D1 (EFHD1) | 1.471193 | Cytoplasm |
| 15. Bone morphogenetic protein 6 (BMP6) | 1.467169 | Extracellular space |
| 16. Growth arrest-specific 6 (GAS6) | 1.4661 | Extracellular space |
| 17. Transmembrane protein 119 (TMEM119) | 1.448072 | Cytoplasm |
| 18. Indolethylamine N-methyltransferase (INMT) | 1.443319 | Cytoplasm |
| 19. Collagen, type VIII, α 1, transcript variant 2 (COL8A1) | 1.43957 | Extracellular space |
| 20. Thioredoxin domain containing 5, transcript variant 2 (TXNDC5) | 1.428763 | Cytoplasm |
| 21. Chemokine (C-C motif) ligand 2 (CCL2) | −2.210669 | Extracellular space |
| 22. Retinoic acid receptor responder (tazarotene induced) 1, transcript variant 1, (RARRES1) | −2.14593 | Plasma membrane |
| 23. Complement factor B (CFB) | −1.834816 | Extracellular space |
| 24. Retinoic acid receptor responder (tazarotene induced) 1, transcript variant 2, (RARRES1) | −1.809309 | Plasma membrane |
| 25. Latexin (LXN) | −1.778936 | Cytoplasm |
| 26. Superoxide dismutase 2, mitochondrial, transcript variant 2, (SOD2) | −1.777997 | Cytoplasm |
| 27. ABI gene family, member 3 (NESH) binding protein (ABI3BP) | −1.635895 | Extracellular space |
| 28. Hypothetical protein FLJ40504 (FLJ40504) | −1.624674 | Unknown |
| 29. Filaggrin (FLG) | −1.589886 | Cytoplasm |
| 30. Claudin 11 (oligodendrocyte transmembrane protein) (CLDN11) | −1.544349 | Plasma membrane |
| 31. PREDICTED: similar to LYPDC1 protein (LOC100134073) | −1.535828 | Plasma membrane |
| 32. DNA-damage regulated autophagy modulator 1 (DRAM1) | −1.535214 | Cytoplasm |
| 33. PREDICTED: miscRNA (LOC399965) | −1.533878 | Unknown |

TABLE 3-continued

Forty most highly differentially regulated genes in VSMCs treated by ETO according to whole genome microarray analysis using Illumina HumanHT-12 v4 expression BeadChip kit.

| Gene name (symbol) | Fold-change | Location |
| --- | --- | --- |
| 34. Potassium voltage-gated channel, shaker-related subfamily, 0 member 1, transcript variant2 (KCNAB1) | −1.491701 | Plasma membrane |
| 35. Pleckstrin homology-like domain, family A, member 1 (PHLDA1) | −1.486817 | Cytoplasm |
| 36. PREDICTED: similar to filaggrin (LOC730833) | −1.473802 | Cytoplasm |
| 37. Transmembrane 4 L six family member 1 (TM4SF1) | −1.466677 | Plasma membrane |
| 38. LY6/PLAUR domain containing 1, transcript variant 1 (LYPD1) | −1.447292 | Plasma membrane |
| 39. Mitogen-activated protein kinase kinase 2 (MAP2K2) | −1.436733 | Cytoplasm |
| 40. Endoglin (Osler-Rendu-Weber syndrome 1) (ENG) | −1.427603 | Cytoplasm |

TABLE 4

Forty most highly differentially regulated genes in VSMCs treated by P4 according to whole genome microarray analysis using Illumina HumanHT-12 v4 expression BeadChip kit.

| Gene name (symbol) | Fold-change | Location |
| --- | --- | --- |
| 1. Homo sapiens thioredoxin domain containing 5, transcript variant 2 (TXNDC5) | 1.361455 | Cytoplasm |
| 2. Cyclin C, transcript variant 2 (CCNC) | 1.343111 | Nucleus |
| 3. Hypoxia-inducible factor 1, a subunit, transcript variant 1 (HIF1A) | 1.327525 | Nucleus |
| 4. Eukaryotic translation initiation factor 4 gamma, 2, transcript variant 1 (EIF4G2) | 1.300035 | Cytoplasm |
| 5. Armadillo repeat containing, X-linked 3, transcript variant 2 (ARMCX3) | 1.29842 | Cytoplasm |
| 6. Sterol-C4-methyl oxidase-like, transcript variant 1 (SC4MOL) | 1.295691 | Cytoplasm |
| 7. Integrin beta 1, transcript variant 1C-2 (ITGB1) | 1.292955 | Plasma membrane |
| 8. Ubiquitin-like modifier activating enzyme 3, transcript variant 2 (UBA3) | 1.29282 | Cytoplasm |
| 9. Janus kinase 1 (JAK1) | 1.29168 | Cytoplasm |
| 10. Armadillo repeat containing, X-linked 3, transcript variant 2 (ARMCX3) | 1.283788 | Cytoplasm |
| 11. Interleukin 33 (IL33) | 1.275012 | Extracellular space |
| 12. cDNA FLJ20769 fis, clone COL06674 (PREDICTED: Receptor tyrosine kinase-like orphan receptor 1) | 1.271463 | Plasma membrane |
| 13. Complement factor H, transcript variant 2 (CFH) | 1.270748 | Extracellular space |
| 14. Keratin 34 (KRT34) | 1.267712 | Cytoplasm |
| 15. PREDICTED: misc_RNA (LOC100131609) | 1.26569 | Unknown |
| 16. Solute carrier family 44, member 1 (SLC44A1) | 1.259625 | Plasma membrane |
| 17. Ring finger protein 11 (RNF11) | 1.256483 | Nucleus |
| 18. Thioredoxin reductase 1, transcript variant 4 (TXNRD1) | 1.254846 | Cytoplasm |
| 19. Serum amyloid A1 transcript variant 2 (SAA1) | −1.566488 | Extracellular space |
| 20. Hypothetical gene supported by AK125735 (LOC441087) | −1.46696 | Unknown |
| 21. Superoxide dismutase 2, mitochondrial transcript variant 2 (SOD2) | −1.361754 | Cytoplasm |
| 22. Hypothetical LOC100190938 (LOC100190938), transcript variant 2, noncoding RNA | −1.358297 | Unknown |
| 23. Mitogen-activated protein kinase kinase 2 (MAP2K2) | −1.346346 | Cytoplasm |
| 24. Serum amyloid A1, transcript variant 1 (SAA1) | −1.324277 | Extracellular space |
| 25. Minichromosome maintenance complex component 8, transcript variant 1 (MCM8) | −1.320138 | Nucleus |
| 26. Complement factor B (CFB) | −1.309157 | Extracellular space |
| 27. N-deacetylase/N-sulfotransferase (heparan glucosaminyl) 1 (NDST1) | −1.306017 | Cytoplasm |

TABLE 4-continued

Forty most highly differentially regulated genes in VSMCs treated by P4 according to whole genome microarray analysis using Illumina HumanHT-12 v4 expression BeadChip kit.

| Gene name (symbol) | Fold-change | Location |
| --- | --- | --- |
| 28. Fukutin, transcript variant 2 (FKiTN) | −1.298799 | Extracellular space |
| 29. Retinoic acid receptor responder (tazarotene induced) 1, transcript variant 2 (RARRES1) | −1.289499 | Plasma membrane |
| 30. Chemokine (C-C motif) ligand 2 (CCL2) | −1.289422 | Extracellular space |
| 31. Polyribonucleotide nucleotidyltransferase 1 (PNPT1) | −1.28606 | Cytoplasm |
| 32. Chromosome 9 ORF 167 (C9orf167) | −1.283051 | Unknown |
| 33. G protein-coupled receptor 1 (GPR1) | −1.282961 | Plasma membrane |
| 34. OCIA domain containing 1, transcript variant 5 (OCIAD1) | −1.274509 | Cytoplasm |
| 35. Retinoic acid receptor responder (tazarotene induced) 1, transcript variant 1 (RARRES1) | −1.271303 | Plasma membrane |
| 36. Hypothetical protein FLJ40504 (FLJ40504) | −1.270468 | Unknown |
| 37. Microtubule-associated protein 1A (MAP1A) | −1.268813 | Cytoplasm |
| 38. Paralemmin, transcript variant 1 (PALM) | −1.259738 | Plasma membrane |
| 39. Zinc finger protein 682, transcript variant 1 (ZNF682) | −1.253921 | Nucleus |
| 40. Staphylococcal nuclease and tudor domain containing 1 (SN D1) | −1.250393 | Nucleus |

EXEMPLIFIED EMBODIMENTS

Examples of embodiments of the invention include, but are not limited to:

Embodiment 1

A method for inhibiting abnormal uterine bleeding (AUB), comprising administering an effective amount of chemokine (C-C motif) ligand 2 (CCL2), or a biologically active fragment thereof, to a subject in need thereof.

Embodiment 2

The method of embodiment 1, wherein the AUB is long acting progestin-only contraceptive (LAPC)-induced.

Embodiment 3

The method of embodiment 2, wherein the LAPC comprises medroxyprogesterone acetate (MPA) or etonogestrel (ETO).

Embodiment 4

The method of embodiment 2 or 3, wherein the LAPC is administered orally, by injection, transdermally, or via implant.

Embodiment 5

The method of any one of embodiments 2 to 4, wherein the LAPC is an injectable form of medroxyprogesterone acetate (MPA; e.g., Depo-Provera), or is administered via a subdermally implanted rod that releases etonogestrel (ETO; e.g., Implanon).

Embodiment 6

The method of any preceding embodiment, wherein the subject has AUB at the time of said administering.

Embodiment 7

The method of any one of embodiments 1 to 5, wherein the subject does not have AUB at the time of said administering, and wherein the CCL2 is administered prophylactically to prevent or delay the onset of the AUB.

Embodiment 8

The method of any preceding embodiment, wherein said administering comprises administering CCL2 polypeptide, or a biologically active fragment of the full-length CCL polypeptide, to the subject.

Embodiment 9

The method of any one of embodiments 1 to 7, wherein said administering comprises administering a nucleic acid encoding the full-length CCL-2 polypeptide, or encoding a biologically active fragment of the full-length CCL-2 polypeptide, to the subject (e.g., via a viral vector or non-viral vector).

Embodiment 10

The method of embodiment 8, wherein the full-length CCL2 polypeptide comprises amino acids 24-99 of SEQ ID NO:1.

Embodiment 11

The method of embodiment 9, wherein the full-length CCL2 polypeptide comprises amino acids 24-99 of SEQ ID NO:1.

Embodiment 12

The method of any preceding embodiment, wherein the CCL2, or biologically active fragment thereof, is administered orally, rectally, transmucosally, intestinally, parenter-

Embodiment 13

A pharmaceutical composition comprising chemokine (C-C motif) ligand 2 (CCL2), or a biologically active fragment thereof; and (a) a long-acting progestin-only contraceptive, or (b) another agent that inhibits abnormal uterine bleeding, or both (a) and (b).

Embodiment 14

The pharmaceutical composition of embodiment 13, wherein the composition is in a dosage form for oral, injectable, or transdermal delivery.

Embodiment 15

A kit for inhibiting abnormal uterine bleeding, comprising chemokine (C-C motif) ligand 2 (CCL2), or a biologically active fragment thereof; and (a) a long-acting progestin-only contraceptive, or (b) another agent that inhibits abnormal uterine bleeding, or both (a) and (b).

Embodiment 16

The kit of embodiment 15, further comprising instructions for use.

REFERENCES

1. Krikun G, et al. (2011) Long-term progestin-only contraception in humans versus animal models. Ann N Y Acad Sci 1221:119-123.
2. Lockwood C J (2011) Mechanisms of normal and abnormal endometrial bleeding. Menopause 18(4):408-411.
3. Affandi B (2002) Long-acting progestogens. Best Pract Res Clin Obstet Gynaecol 16(2): 169-179.
4. Lockwood C J, Schatz F, Krikun G (2004) Angiogenic factors and the endometrium following long term progestin only contraception. Histol Histopathol 19(1):167-172.
5. Carter A M (2007) Animal models of human placentation-A review. Placenta 28(Suppl A):S41-S47.
6. Hutz R J, Bejvan S M, Durning M, Dierschke D J (1990) Changes in follicular populations, in serum estrogen and progesterone, and in ovarian steroid secretion in vitro during the guinea pig estrous cycle. Biol Reprod 42(2): 266-272.
7. Lee K Y, DeMayo F J (2004) Animal models of implantation. Reproduction 128(6):679-695.
8. Krikun G, et al. (2012) Effects of etonogestrel treatment in the reproductive organs and uterine arteries of nonoophorectomized guinea pigs. Reprod Sci 19(4):400-406.
9. Krikun G, et al. (2010) Long-term progestin contraceptives (LTPOC) induce aberrant angiogenesis, oxidative stress and apoptosis in the guinea pig uterus: A model for abnormal uterine bleeding in humans. J Angiogenes Res 2:8.
10. Lockwood C J, Krikun G, Hickey M, Huang S J, Schatz F (2009) Decidualized human endometrial stromal cells mediate hemostasis, angiogenesis, and abnormal uterine bleeding. Reprod Sci 16(2):162-170.
11. Carmeliet P (2000) Mechanisms of angiogenesis and arteriogenesis. Nat Med 6(4):389-395.
12. Ribatti D, Nico B, Crivellato E (2011) The role of pericytes in angiogenesis. Int J Dev Biol 55(3):261-268.
13. Hellström M, Kalén M, Lindahl P, Abramsson A, Betsholtz C (1999) Role of PDGF-B and PDGFR-beta in recruitment of vascular smooth muscle cells and pericytes during embryonic blood vessel formation in the mouse. Development 126(14):3047-3055.
14. Hickey M, et al. (2006) Long-term progestin-only contraceptives result in reduced endometrial blood flow and oxidative stress. J Clin Endocrinol Metab 91(9):3633-3638.
15. Kim D K, Zhang L, Dzau V J, Pratt R E (1994) H19, a developmentally regulated gene, is reexpressed in rat vascular smooth muscle cells after injury. J Clin Invest 93(1):355-360.
16. Selzman C H, et al. (2002) Monocyte chemotactic protein-1 directly induces human vascular smooth muscle proliferation. Am J Physiol Heart Circ Physiol 283(4): H1455-H1461.
17. Tanaka K, et al. (2012) Interaction of Tmem119 and the bone morphogenetic protein pathway in the commitment of myoblastic into osteoblastic cells. Bone 51(1):158-167.
18. Wang X, et al. (2013) TIG1 promotes the development and progression of inflammatory breast cancer through activation of Axl kinase. Cancer Res 73(21):6516-6525.
19. Mowen K A, et al. (2001) Arginine methylation of STAT1 modulates IFNalpha/betainduced transcription. Cell 104(5):731-741.
20. Hickey M, Dwarte D, Fraser I S (2000) Superficial endometrial vascular fragility in Norplant users and in women with ovulatory dysfunctional uterine bleeding. Hum Reprod 15(7):1509-1514.
21. Abberton K M, Healy D L, Rogers P A (1999) Smooth muscle alpha actin and myosin heavy chain expression in the vascular smooth muscle cells surrounding human endometrial arterioles. Hum Reprod 14(12):3095-3100.
22. Kohnen G, Campbell S, Jeffers M D, Cameron I T (2000) Spatially regulated differentiation of endometrial vascular smooth muscle cells. Hum Reprod 15(2):284-292.
23. Rogers P A, Plunkett D, Affandi B (2000) Perivascular smooth muscle alpha-actin is reduced in the endometrium of women with progestin-only contraceptive breakthrough bleeding. Hum Reprod 15 (Suppl 3):78-84.
24. Abberton K M, Taylor N H, Healy D L, Rogers P A (1999) Vascular smooth muscle cell proliferation in arterioles of the human endometrium. Hum Reprod 14(4): 1072-1079.
25. Lash G E, et al. (2012) Localization of angiogenic growth factors and their receptors in the human endometrium throughout the menstrual cycle and in recurrent miscarriage. Hum Reprod 27(1):183-195.
26. Levéen P, et al. (1994) Mice deficient for PDGF B show renal, cardiovascular, and hematological abnormalities. Genes Dev 8(16):1875-1887.
27. Soriano P (1994) Abnormal kidney development and hematological disorders in PDGF beta-receptor mutant mice. Genes Dev 8(16):1888-1896.
28. Lee W S, Harder J A, Yoshizumi M, Lee M E, Haber E (1997) Progesterone inhibits arterial smooth muscle cell proliferation. Nat Med 3(9):1005-1008.
29. Watanabe T, Pakala R, Katagiri T, Benedict C R (2001) Monocyte chemotactic protein 1 amplifies serotonin-induced vascular smooth muscle cell proliferation. J Vasc Res 38(4):341-349.

30. Spinetti G, et al. (2004) Rat aortic MCP-1 and its receptor CCR2 increase with age and alter vascular smooth muscle cell function. Arterioscler Thromb Vasc Biol 24(8): 1397-1402.
31. Hayes I M, et al. (1998) Human vascular smooth muscle cells express receptors for CC chemokines. Arterioscler Thromb Vasc Biol 18(3):397-403.
32. Seki Y, et al. (2000) Role of the JAK/STAT pathway in rat carotid artery remodeling after vascular injury. Circ Res 87(1):12-18.
33. Hu X, Park-Min K H, Ho H H, Ivashkiv L B (2005) IFN-gamma-primed macrophages exhibit increased CCR2-dependent migration and altered IFN-gamma responses mediated by Stat1. J Immunol 175(6):3637-3647.
34. Budwit-Novotny D A, et al. (1986) Immunohistochemical analyses of estrogen receptor in endometrial adenocarcinoma using a monoclonal antibody. Cancer Res 46(10):5419-5425.
35. Guzeloglu-Kayisli 0, et al. (2014) Long-acting progestin-only contraceptives enhance human endometrial stromal cell expressed neuronal pentraxin-1 and reactive oxygen species to promote endothelial cell apoptosis. J Clin Endocrinol Metab 99(10):E1957-E1966.
36. Lockwood C J, et al. (2014) Interferon-γ protects first-trimester decidual cells against aberrant matrix metalloproteinases 1, 3, and 9 expression in preeclampsia. Am J Pathol 184(9):2549-2559.
37. Collins, J., Crosignani, P. G., et. al. Hormonal contraception without estrogens. Hum Reprod Update 2003, 9:373-386.
38. Mulvany, M. J., and Aalkjaer, C. Structure and function of small arteries. Physiol Rev 1990, 70:921-961.
39. Rogers, P. A., and Abberton, K. M. Endometrial arteriogenesis: vascular smooth muscle cell proliferation and differentiation during the menstrual cycle and changes associated with endometrial bleeding disorders. Microsc Res Tech 2003, 60:412-419.

We claim:

1. A method for reversing long acting progestin-only contraceptive (LAPC)-induced inhibition of vascular smooth muscle cell (VSMC) proliferation in a subject, comprising administering an effective amount of chemokine (C-C motif) ligand 2 (CCL2) and the LAPC to the subject, wherein the CCL2 comprises a CCL2 polypeptide comprising amino acids 24-99 of SEQ ID NO: 1.

2. The method of claim 1, wherein the LAPC comprises medroxyprogesterone acetate (MPA) or etonogestrel (ETO).

3. The method of claim 1, wherein the LAPC is administered orally, by injection, transdermally, via implant, or via intrauterine device (IUD).

4. The method of claim 1, wherein the LAPC is an injectable form of medroxyprogesterone acetate (MPA), or is administered via a subdermally implanted rod that releases etonogestrel (ETO).

5. The method of claim 1, wherein the subject has LAPC-induced abnormal uterine bleeding (AUB) at the time of said administering.

6. The method of claim 1, wherein the subject does not have LAPC-induced abnormal uterine bleeding (AUB) at the time of said administering.

7. The method of claim 1, wherein the CCL2 is administered orally, rectally, transmucosally, intestinally, parenterally, intramuscularly, subcutaneously, intravenously, intraperitoneally, intranasally, intravaginally, intrauterineally, or intraocularly.

8. The method of claim 1, wherein the CCL2 is administered locally.

9. The method of claim 1, wherein the CCL2 is administered intravaginally or intrauterineally.

10. A composition comprising an effective amount of chemokine (C-C motif) ligand 2 (CCL2); and a long-acting progestin-only contraceptive, wherein the CCL2 comprises a CCL2 polypeptide comprising amino acids 24-99 of SEQ ID NO: 1.

SEQUENCE LISTING

```
<160> NUMBER OF SEQ ID NOS: 1

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

11. The composition of claim 10, wherein the composition is in the form of a patch, implant, intrauterine device, or vaginal ring.

12. The composition of claim 10, wherein the composition is in the form of a tablet, pill, dragee, capsules, liquid, gel, syrup, slurry, or suspension.

13. A kit, comprising one or more containers holding, separately or together: an effective amount of chemokine (C-C motif) ligand 2 (CCL2); and a long-acting progestin-only contraceptive, wherein the CCL2 comprises a CCL2 polypeptide comprising amino acids 24-99 of SEQ ID NO: 1.

* * * * *